United States Patent
Meltzer et al.

(10) Patent No.: US 12,241,059 B2
(45) Date of Patent: Mar. 4, 2025

(54) TIERED LIGATION OLIGOS

(71) Applicant: ILLUMINA, INC., San Diego, CA (US)

(72) Inventors: Robert Meltzer, Belmont, MA (US); Kristina Fontanez, Arlington, MA (US); Yi Xue, Shrewsbury, MA (US)

(73) Assignee: Illumina, Inc., San Diego, CA (US)

( * ) Notice: Subject to any disclaimer, the term of this patent is extended or adjusted under 35 U.S.C. 154(b) by 65 days.

(21) Appl. No.: 17/376,709

(22) Filed: Jul. 15, 2021

(65) Prior Publication Data

US 2022/0017892 A1   Jan. 20, 2022

Related U.S. Application Data

(60) Provisional application No. 63/052,073, filed on Jul. 15, 2020.

(51) Int. Cl.
*C12N 15/10* (2006.01)
*C12Q 1/6853* (2018.01)

(52) U.S. Cl.
CPC ....... *C12N 15/1065* (2013.01); *C12Q 1/6853* (2013.01)

(58) Field of Classification Search
CPC . C12N 15/1065; C12Q 1/6853; C12Q 1/6806
See application file for complete search history.

(56) References Cited

U.S. PATENT DOCUMENTS

| | | |
|---|---|---|
| 4,701,415 A | 10/1987 | Dutton |
| 5,512,439 A | 4/1996 | Hornes et al. |
| 5,813,759 A | 9/1998 | Gebrian |
| 6,210,891 B1 | 4/2001 | Nyren et al. |
| 6,306,597 B1 | 10/2001 | Macevicz |
| 6,309,833 B1 | 10/2001 | Edman et al. |
| 6,828,100 B1 | 12/2004 | Ronaghi |
| 6,833,246 B2 | 12/2004 | Balasubramanian |
| 6,911,345 B2 | 6/2005 | Quake et al. |
| 7,232,656 B2 | 6/2007 | Balasubramanian et al. |
| 7,537,897 B2 | 5/2009 | Brenner et al. |
| 7,598,035 B2 | 10/2009 | Macevicz |
| 7,835,871 B2 | 11/2010 | Kain et al. |
| 7,842,457 B2 | 11/2010 | Berka et al. |
| 7,960,120 B2 | 6/2011 | Rigatti et al. |
| 8,012,690 B2 | 9/2011 | Berka et al. |
| 8,629,323 B2 | 1/2014 | Weeks |
| 8,715,934 B2 | 5/2014 | Diehl et al. |
| 8,748,102 B2 | 6/2014 | Berka et al. |
| 8,765,380 B2 | 7/2014 | Berka et al. |
| 9,011,777 B2 | 4/2015 | Beer |
| 9,012,390 B2 | 4/2015 | Holtze et al. |
| 9,085,798 B2 | 7/2015 | Chee |
| 9,260,751 B2 | 2/2016 | Diehl et al. |
| 9,388,465 B2 | 7/2016 | Hindson et al. |
| 9,399,797 B2 | 7/2016 | Hutchison et al. |
| 9,562,837 B2 | 2/2017 | Link |
| 9,567,645 B2 | 2/2017 | Fan et al. |
| 9,567,646 B2 | 2/2017 | Fan et al. |
| 9,580,736 B2 | 2/2017 | Tan et al. |
| 9,598,736 B2 | 3/2017 | Fan et al. |
| 9,637,799 B2 | 5/2017 | Fan et al. |
| 9,650,629 B2 | 5/2017 | Froehlich et al. |
| 9,695,474 B2 | 7/2017 | Johnson et al. |
| 9,701,998 B2 | 7/2017 | Hindson et al. |
| 9,708,654 B2 | 7/2017 | Hunicke-Smith et al. |
| 9,783,847 B2 | 10/2017 | Chee |
| 9,951,386 B2 | 4/2018 | Hindson et al. |
| 10,030,267 B2 | 7/2018 | Hindson et al. |
| 10,041,116 B2 | 8/2018 | Hindson et al. |
| 10,131,958 B1 | 11/2018 | Fan et al. |
| 10,151,003 B2 | 12/2018 | Fan et al. |
| 10,155,981 B2 | 12/2018 | Brenner et al. |
| 10,202,628 B2 | 2/2019 | Church et al. |
| 10,208,356 B1 | 2/2019 | Fan et al. |
| 10,221,442 B2 | 3/2019 | Hindson et al. |
| 10,240,192 B2 | 3/2019 | Berka et al. |

(Continued)

FOREIGN PATENT DOCUMENTS

| | | |
|---|---|---|
| AU | 2013203624 A1 | 5/2013 |
| EP | 3467160 A1 | 4/2019 |

(Continued)

OTHER PUBLICATIONS

Rosenberg et. al. Single-cell profiling of the developing mouse brain and spinal cord with split-pool barcoding. Science (2018) vol. 360, Issue 6385, pp. 176-182. https://www.science.org/doi/10.1126/science.aam8999 (Year: 2018).*
Fan, 2017, Barcode Doublets, JEFWorksLab (5 pages).
Int Search Report and Written Op mailed: Nov. 23, 2021, for Int Application No. PCT/US2021/41810, filed Jul. 15, 2021 (23 pages).
Jacobsen, 2004, Direct isolation of poly(A)+ RNA from 4 M guanidine thiocyanate-lysed cell extracts using locked nucleic acid-oligo(T) capture, Nucleic Acids Research, 32(7), 10 pages.
Klein, 2015, Droplet barcoding for single cell transcriptomics applied to embryonic stem cells, Cells, 161(5):1187-1201.
Bowman, 2013, Multiplexed Illumina sequencing libraries from picogram quantities of DNA, BMC Genomics 14:466 (8 pages).
Eastbum, 2013, Ultrahigh-trhoughput mammalian single-cell reverse-transcriptase polymerase chain reaction in microfluidic drops, Anal Chem 85:8016-8021.
Figueiredo, 2007, Cost effective method for construction of high quality cDNA libraries, Biomol Eng 24:419-421.

(Continued)

*Primary Examiner* — Nancy J Leith
*Assistant Examiner* — Jessica D Parisi
(74) *Attorney, Agent, or Firm* — Illumina, Inc.

(57) ABSTRACT

The disclosure provides methods for creating long oligonucleotide reagents that include barcodes and other element for sequencing library preparation, where the oligonucleotides are created by multiple tiers of ligation of shorter oligos. The disclosed methods work to extend short oligos that are attached to particles, thereby allowing one to create particles that carry large number of long sample preparation oligonucleotides without being required to synthesize those full-length molecules with a polymerase.

19 Claims, 17 Drawing Sheets

(56) References Cited

U.S. PATENT DOCUMENTS

| | | |
|---|---|---|
| 10,240,197 B1 | 3/2019 | Brenner et al. |
| 10,253,375 B1 | 4/2019 | Fan et al. |
| 10,266,883 B2 | 4/2019 | Chee |
| 10,280,459 B1 | 5/2019 | Brenner et al. |
| 10,285,940 B2 | 5/2019 | Mason et al. |
| 10,329,557 B2 | 6/2019 | Johnson et al. |
| 10,344,329 B2 | 7/2019 | Hindson et al. |
| 10,392,662 B1 | 8/2019 | Brenner et al. |
| 10,400,280 B2 | 9/2019 | Hindson et al. |
| 10,415,030 B2 | 9/2019 | Marshall et al. |
| 10,457,986 B2 | 10/2019 | Hindson et al. |
| 10,501,793 B2 | 12/2019 | Chee |
| 10,584,381 B2 | 3/2020 | Hindson et al. |
| 11,060,149 B2 | 7/2021 | Steelman |
| 11,104,961 B2 | 8/2021 | Fontanez et al. |
| 11,142,791 B2 | 10/2021 | Abate et al. |
| 2002/0132251 A1 | 9/2002 | Shuber |
| 2003/0143599 A1 | 7/2003 | Makarov et al. |
| 2003/0180737 A1 | 9/2003 | Gu et al. |
| 2004/0005585 A1 | 1/2004 | Bi et al. |
| 2006/0024681 A1 | 2/2006 | Smith et al. |
| 2006/0177836 A1 | 8/2006 | McKernan et al. |
| 2006/0292611 A1 | 12/2006 | Berka et al. |
| 2007/0080316 A1 | 4/2007 | Sauer et al. |
| 2007/0114362 A1 | 5/2007 | Feng et al. |
| 2008/0004436 A1 | 1/2008 | Tawfik |
| 2009/0280475 A1 | 11/2009 | Pollack et al. |
| 2011/0009278 A1 | 1/2011 | Kain et al. |
| 2011/0086780 A1 | 4/2011 | Colston, Jr. et al. |
| 2011/0118151 A1 | 5/2011 | Eshoo et al. |
| 2011/0311978 A1 | 12/2011 | Makarewicz, Jr. et al. |
| 2012/0295269 A1 | 11/2012 | Pourahmadi et al. |
| 2012/0316074 A1 | 12/2012 | Saxonov |
| 2013/0115169 A1 | 5/2013 | Lahann et al. |
| 2014/0155295 A1 | 6/2014 | Hindson et al. |
| 2014/0228255 A1* | 8/2014 | Hindson ............ C12N 15/1065 506/26 |
| 2015/0133312 A1 | 5/2015 | Bielas et al. |
| 2015/0225777 A1 | 8/2015 | Hindson et al. |
| 2016/0186267 A1 | 6/2016 | So et al. |
| 2016/0250608 A1 | 9/2016 | Anders et al. |
| 2016/0274103 A1 | 9/2016 | Piloto et al. |
| 2017/0192030 A1 | 7/2017 | Lapham et al. |
| 2017/0218437 A1 | 8/2017 | Seul et al. |
| 2017/0232417 A1 | 8/2017 | Lebofsky et al. |
| 2017/0255160 A1 | 9/2017 | Numata et al. |
| 2018/0010105 A1 | 1/2018 | Rogers et al. |
| 2018/0051321 A1* | 2/2018 | Hindson ............ C12N 15/1065 |
| 2018/0119216 A1 | 5/2018 | Jamshidi et al. |
| 2018/0133715 A1 | 5/2018 | Craig et al. |
| 2018/0179553 A1 | 6/2018 | Watson et al. |
| 2018/0216162 A1 | 8/2018 | Belhocine et al. |
| 2018/0237836 A1 | 8/2018 | Abate et al. |
| 2018/0274027 A1 | 9/2018 | Hindson et al. |
| 2018/0355407 A1 | 12/2018 | Utharala et al. |
| 2019/0085412 A1 | 3/2019 | Fan et al. |
| 2019/0153532 A1 | 5/2019 | Bharadwaj et al. |
| 2019/0153550 A1 | 5/2019 | Steinmetzer et al. |
| 2019/0177789 A1 | 6/2019 | Hindson et al. |
| 2019/0203262 A1 | 7/2019 | Hindson et al. |
| 2019/0316197 A1 | 10/2019 | Hindson et al. |
| 2019/0323003 A1 | 10/2019 | Ramji et al. |
| 2019/0323091 A1 | 10/2019 | Bramlett et al. |
| 2019/0338353 A1 | 11/2019 | Belgrader et al. |
| 2019/0352714 A1 | 11/2019 | Salk et al. |
| 2019/0381497 A1 | 12/2019 | DiCarlo et al. |
| 2019/0382753 A1 | 12/2019 | Steemers et al. |
| 2020/0040385 A1 | 2/2020 | Beechem et al. |
| 2020/0080112 A1 | 3/2020 | Zhang et al. |
| 2020/0123582 A1 | 4/2020 | Tan et al. |
| 2020/0190513 A1 | 6/2020 | Fernandez et al. |
| 2020/0261879 A1 | 8/2020 | Abate et al. |
| 2020/0324287 A1 | 10/2020 | Vijayan et al. |
| 2020/0376488 A1 | 12/2020 | Wu et al. |
| 2021/0010070 A1 | 1/2021 | Schnall-Levin et al. |
| 2021/0054369 A1 | 2/2021 | Meltzer et al. |
| 2021/0214721 A1 | 7/2021 | Fontanez et al. |
| 2021/0214763 A1 | 7/2021 | Fontanez et al. |
| 2021/0214769 A1 | 7/2021 | Fontanez et al. |
| 2021/0214792 A1 | 7/2021 | Fontanez et al. |
| 2021/0214802 A1 | 7/2021 | Fontanez et al. |
| 2021/0215591 A1 | 7/2021 | Fontanez et al. |
| 2021/0301354 A1 | 9/2021 | Kiani |
| 2021/0332432 A1 | 10/2021 | Kiani |
| 2021/0340596 A1 | 11/2021 | Meltzer et al. |
| 2021/0381064 A1 | 12/2021 | Fontanez et al. |
| 2022/0017892 A1 | 1/2022 | Meltzer et al. |
| 2022/0135966 A1 | 5/2022 | Meltzer |
| 2022/0136071 A1 | 5/2022 | Meltzer |
| 2022/0154248 A1 | 5/2022 | Abate et al. |
| 2022/0235416 A1 | 7/2022 | Fontanez et al. |
| 2022/0267761 A1 | 8/2022 | Fontanez et al. |

FOREIGN PATENT DOCUMENTS

| | | |
|---|---|---|
| EP | 3819637 A1 | 5/2021 |
| JP | 2021072863 A | 5/2021 |
| WO | 1997/008547 A1 | 3/1997 |
| WO | 2010/117620 A2 | 10/2010 |
| WO | 2011/047307 A1 | 4/2011 |
| WO | 2012/116146 A1 | 8/2012 |
| WO | 2012/149042 A2 | 11/2012 |
| WO | 2013/165748 A1 | 11/2013 |
| WO | 2014/028537 A1 | 2/2014 |
| WO | 2014/100434 A1 | 6/2014 |
| WO | 2014/146025 A1 | 9/2014 |
| WO | 2014/153071 A1 | 9/2014 |
| WO | 2015/157369 A1 | 10/2015 |
| WO | 2015/187792 A1 | 12/2015 |
| WO | 2016/025815 A1 | 2/2016 |
| WO | 2016/040476 A1 | 3/2016 |
| WO | 2016/126871 A2 | 8/2016 |
| WO | 2016/138080 A1 | 9/2016 |
| WO | 2016/172373 A1 | 10/2016 |
| WO | 2017/161306 A1 | 9/2017 |
| WO | 2019/011971 A1 | 1/2019 |
| WO | 2019/023627 A1 | 1/2019 |
| WO | 2019/139650 A2 | 7/2019 |
| WO | 2019/157529 A1 | 8/2019 |
| WO | 2019/204229 A1 | 10/2019 |
| WO | 2019/217552 A1 | 11/2019 |
| WO | 2019/222523 A2 | 11/2019 |
| WO | 20200037214 A1 | 2/2020 |
| WO | 2020/069268 A1 | 4/2020 |
| WO | 2020/069298 A1 | 4/2020 |

OTHER PUBLICATIONS

Fu, 2015, Uniform and accurate single-cell sequencing based on emulsion whole-genome amplification, PNAS 112(38):11923-11928.

Hatori, 2019, Particle-Templated Emulsification for Microfluidics-Free Digital Biology, Analytical Chemistry, 90:9813-9820.

Int Search Report and Written Op mailed Apr. 1, 2021, for Int Application No. PCT/US2021/013069, filed Jan. 12, 2021 (14 pages).

Int Search Report and Written Op mailed Aug. 11, 2021, for Int Application No. PCT/US2021/022503, filed Mar. 16, 2021 (9 pages).

Int Search Report and Written Op mailed Feb. 2, 2021, for Int Application No. PCT/US2020/47214, filed Aug. 20, 2020 (14 pages).

Int Search Report and Written Op mailed Jun. 30, 2021, for Int Application No. PCT/US2021/023815, filed Mar. 24, 2021 (14 pages).

Int Search Report and Written Op mailed Mar. 29, 2021, for Int Application No. PCT/US2021/013042, filed Jan. 12, 2021 (9 pages).

Int Search Report and Written Op mailed Mar. 29, 2021, for Int Application No. PCT/US2021/013045, filed Jan. 12, 2021 (8 pages).

Int Search Report and Written Op mailed Mar. 29, 2021, for Int Application No. PCT/US2021/013065, filed Jan. 12, 2021 (11 pages).

(56) References Cited

OTHER PUBLICATIONS

Int Search Report and Written Op mailed Mar. 29, 2021, for Int Application No. PCT/US2021/013066, filed Jan. 12, 2021 (11 pages).
Int Search Report and Written Op mailed Mar. 31, 2021, for Int Application No. PCT/US2021/013048, filed Jan. 12, 2021 (20 pages).
Kumaresan, 2008, High-throughput single copy DNA amplification and cell analysis in engineered nanoliter droplets, Anal Chem, 80:3522-3529.
Kumari, 2017, Quantification of Circulating Free DNA as a Diagnostic Marker in Gall Bladder Cancer, Pathology & Oncology Research, 23:91-97.
Lage, 2003, Whole genome analysis of genetic alterations in small DNA samples using hyperbranched strand displacement amplification and array-CGH, Genome Res 13:294-307.
Lyons, 2017, Large-scale DNA barcode library generation for biomolecule identification in high-throughput screens, Sci Rep 7:13899 (7 pages).
Mazutis, 2013, Singl-cell analysis and sorting using droplet-based microfluidics, Nature Protocols, 8(5):870-891.
Nishikawa, 2015, Monodisperse picoliter droplets for low-bias and contamination-free reactions in single-cell whole genome amplification, PLoSOne 10(9):e0138733 (15 pages).
Roche, 2011, emPCR amplificaiotn method manual, 454 Life Sciences Corp (12 pages).
Sidore, 2016, Enhanced sequencing coverage with digital droplet multiple displacement amplification, Nucl Acids Res 44(7):e66 (9 pages).
Stoeckius, 2017, Simultaneous epitope and transcriptome measurment in single cells, Nat Meth online pub (10 pages).
Tamminen, 2015, Single gene-based distinction of individual microbial genomes from a mixed population of microbial cells Front Microb 6:195 (10 pages).
Vitale, 2019, An Optimized Workflow to Evaluate Estrogen Receptor Gene Mutations in Small Amounts of Cell-Fee DNA, The Journal of Molecular Diagnostics, 21(1):123-127.
Walls, 2020, Structure, Function, and Antigenicity of the SARS-COV-2 Spike Glcoprotein, Cell, 181(2):281-292.
Zilionis, 2016, Single-cell barcoding and sequencing using droplet microfluidics, Natutre Prot 12(1):44-73.
Berensmeier, 2006, Magnetic particles for the separation and purification of necleic acids, Applied Microbiology and Biotechnology, 73:495-504.
Biocompare, 2013, How to maintain a constant temp in your CO2 incubator, Jan. 17, 2013 (Jan. 17, 2013) [online] retrieved from <URL: https://www.biocompare.com/Editorial-Articles/126328-Incubators/#:~text=A jacket of water circulates, thermal buffer against outside air.> entire document, 7 pages.
Brouzes, 2009, Droplet microfluidic technology for single-cell high-throughput screening, Proc Natl Acad Sci 106(34):14195-14200.
Cai, 2019, Selection of DNA-encoded libraries to protein targets within and on living cells, Journal of the American Chemical Society, 141(43):1-11.
Cheng, 2020, Ultra-senstive and rapid detection of nucleic acids and microorganisms in body fluids using single molecule tethering, Nature Communications, 11(1):1-9.
Datlinger, 2017, Pooled CRISPR screening with single-cell transcriptome readout, Nature Methods 4(3):297-301.
High containment laboratories at CDC—Fifty Years of Excellence, Centers for Disease Control and Prevention, etreived from the internet, <https://www.cdc.gov/ncezid/dhcpp/hcl-50/high-containment-laboratories.html>, 1 page.
Kim, 2018, Single-Cell RT-PCR in Microfluidic Droplets with Integrated Chemical Lysis, Anal Chem 90(2):1273-1279.
Kukurba, 2015, RNA Sequencing and Analysis, Cold Spring Harb Protoc 11:951-969.
Markus, 2021, Analysis of recurrently protected genomic regions in cell-free DNA found in urine, Science Translational Medicine, 13(581):1-31.
Patel, 2019, Design and fabrication of low cost vortex mixer using additive manufacturing, International Journal of Applied Engineering Research 14(1):246-249.
Petersen, 2021, Screening of DNA-encoded small molecule libraries inside a living cell, Journal of the American Chemical Society, 143(7):2751-2756.
Quail, 2012, A tale of three next generation sequencing platforms: comparison of Ion Torrent, Pacific Biosciences and Illumina MiSeq sequencers, BMC Genomics 13:341, 13 pages.
Replogle, 2020, Combinatorial single-cell CRISPR screens by direct guide RNA capture and targeted sequencing, Nat. Biotechnol. 38(8):954-961.
Stoeckius, 2017, Large-scale simultaneous measurements of epitopes and transcriptomes in single cells, Nat Methods 14(9):865-868.
Tokunaga, 2013, Systematic exploration of lipophilic tags that allow efficient anchoring of aptamers to live cell surfaces, Chem Lett 42(2):127-129.

* cited by examiner

| | | round 1 | round 2 | round 3 | round 4 | round 5 | barcode combination | collision rate 10k cells |
|---|---|---|---|---|---|---|---|---|
| 2 level | 2 plates | 96 | 96 | | | | 9.22E+03 | 66.21% |
| | 8 plates | 384 | 384 | | | | 1.47E+05 | 6.56% |
| | 24 | 1152 | 1152 | | | | 1.33E+06 | 0.75% |
| | 56 plates | 2688 | 2688 | | | | 7.23E+06 | 0.14% |
| 3 level | 3 plates | 96 | 96 | 96 | | | 8.85E+05 | 1.12% |
| | | 384 | 384 | 96 | | | 3.54E+06 | 0.28% |
| | 6 plates | 192 | 192 | 192 | | | 7.08E+06 | 0.14% |
| | | 5 | 384 | 384 | | | 7.37E+05 | 1.35% |
| 4 level | | 96 | 96 | 96 | 8 | | 7.08E+06 | 0.14% |
| | 3 plates, 8 pips batches | 8 | 96 | 96 | 96 | | 7.08E+06 | 0.14% |
| | | | | | | | | 1M cells |
| 5 level | | 8 | 96 | 96 | 96 | 96 | 6.79E+08 | 0.15% |

PIPs linker code
3-tier combinatorial barcodes
Well specific sample index

FIG. 1

Full barcode anatomy

[T-linker] [PCRsite] [SP1] [barcode1] [RE1] [clamp] [barcode2] [clamp] [RE2] [clamp] [barcode3] [clamp] [RE3] [barcode4] [UMI] [PolyT]

Total Length 141
Barcode length 66

FIG. 5

96x96 with optimized ligation design

[T-linker] [PCRsite] [SP1] [clamp] [barcode1] [clamp] [RE1] [barcode2] [UMI] [PolyT]

FIG. 7

96x96 with optimized ligation design and modular capture moieties

[T-linker] [PCRsite] [SP1] [clamp] [barcode1] [clamp] [RE1] [barcode2] [UMI] [RE2] [PolyT]/[PolyN]/[crisper feature]/[antibody tag]

Modular capture moieties.

Assume that these are added in combination with PolyT

Enables multiomics and perturb seq applications

CTTTTTTTTTTTTTTV
C[10 base complementary sequence?]NNNNNN
C[antibody barcode][smartPCR]
C[Crisper feature capture moiety]

FIG. 8

[5'Acr][T-linker] [SP1] [B1] [L2] [B2] [L3] [B3] [L4] [PIPs batch barcode] [UMI] [Poly-t]

Read 1 barcode sequence structure
5'-[BC1-8bp]-[L1-6 bp]-[C1-1bp]-[BC2-8bp]-[C2-1bp]-[L2 6bp]-[BC3-8bp]-[UMI-12bp]-[polyt]

FIG. 24

TIERED LIGATION OLIGOS

TECHNICAL FIELD

The disclosure relates to tools for understanding gene expression and biology.

BACKGROUND

In living organisms, genetic information is stored in DNA. Genetic information in the DNA is transcribed into messenger RNA (mRNA), which is translated into protein. Proteins play critical functional and structural roles in living organisms. For example, most enzymes are made of proteins, and those enzymes catalyze the metabolic reactions that keep us alive. It is also enzymes that copy DNA into mRNA. Proteins are also structural, and constitute the essential fibers of muscles, the predominant material of hair, as well as basic structural linkages within the cytoskeleton. Essentially, all such proteins are made by translating an mRNA into the protein. In fact, one mRNA can serve as the template for synthesizing multiple copies of a protein.

Because living cells change in response to different environmental conditions, nutrient availability, and even intracellular signaling, the cells need different proteins at different times. The mRNAs that are present in a cell at a given moment could reveal much about how the cell is responding to a pathogen, or a drug, or to age-specific developmental changes.

Most approaches to capturing mRNAs or other nucleic acids use synthetic oligonucleotides for target capture. For example, complementary primers may be introduced to hybridize to, and copy, a target of interest. Many assays involve nucleic acid sequencing, and the capture oligos may have to include numerous long sequences such as sequencing instrument adaptors, index sequences, the primer sequences, primer binding sites for amplification, and restriction sites for downstream handling. Unfortunately, the creation of such reagents typically involves numerous rounds of copying various templates with polymerase, and even hybridizing one template to another and using a polymerase to copy the first into the second. This is problematic because polymerase enzymes are error prone and require complex lab protocols with generous room for error. Other approaches such as solid phase synthesis of long reagent oligos are expensive and require uncommon machinery.

SUMMARY

The disclosure provides methods for creating long oligonucleotide reagents that include barcodes and other elements for sequencing library preparation, where the oligonucleotides are created by multiple tiers of ligation of shorter oligos. The disclosed methods work to extend short oligos that are attached to particles to begin with, thereby allowing one to create particles that carry large numbers of long sample preparation oligonucleotides without being required to synthesize those full-length molecules with a polymerase. In fact, the initial particles may be hydrogels with an acrydite linkage to only a very short linker oligo. Those particles can be incubated with linker duplexes and ligase to extend to the initial short linker oligo. A successive "tier" of incubation can further extend the emerging barcode oligonucleotide. In fact, after just three such tiers of such extension by ligation, sets of the particles can be uniquely barcoded with multiple millions of barcodes. The provided particles with the ligation-based barcode oligonucleotides may be sequestered into fluid partitions with individual cells and used for molecular labeling of the contents of the cells. The long oligonucleotides linked to the particles may be in excess of 100 bases long but are built up without using polymerase. The error and slippage of polymerase are avoided, so the linked oligonucleotides reliably have the intended sequence. Additionally, the ligation-based methods are straightforward to implement using commercially available reagents.

Thus, the disclosure provides ligation-based library manufacture methods. The disclosed methods improve efficiency and quality of barcode libraries grafted to hydrogel particles compared to those form by polymerase or solid-phase synthesis. Precedent split pool chemistry relies on polymerase-based primer extension to sequentially add barcode elements to a linker adaptor grafted to the hydrogel polymer matrix. Those polymerase-based approaches required complex, and inefficient workflow prone to poor yield. Error prone barcodes due to polymerase transcription fidelity, and limited number of total barcodes in the initial design due to limitations of two-tier split pool synthesis. The present disclosure employs multiple tiers of ligation instead of polymerization to link barcoded primers on the hydrogel. These approaches eliminate barcode error due to mis-polymerization. The disclosed methods require minimal manipulation between steps and are faster and more economical than polymerase methods. Methods of the disclosure may include 3 or more sequential reactions and can therefore achieve many more combinatorial barcodes while maintaining excellent separability of barcodes.

In certain aspects, the disclosure provides a method for creating a target capture reagent. The method includes dividing a plurality of initial oligos into a set of partitions; ligating partition-specific first barcodes to the initial oligos to form ligation products; pooling the ligation products into a pool; splitting the pool into a second set of partitions; and ligating partition-specific second barcodes to the ligation products to form tripartite oligonucleotides. Each tripartite oligonucleotide comprises (i) one of the initial oligos, (ii) one of the first barcodes, and (iii) one of the second barcodes. The method may further include pooling and splitting the tripartite oligonucleotides into partitions and ligating partition-specific third barcodes to the tripartite oligonucleotides. Preferably the initial oligos are linked to beads (e.g., hydrogel particles) and the splitting step comprising dividing the beads into the set of partitions. The initial oligoes may be linked to the beads by acrydite linkages. The method may be used to provide a plurality of beads, each linked to a plurality of copies of one of the tripartite oligonucleotides, wherein the tripartite oligonucleotides have been covalently synthesized on the beads using ligase and without using polymerase. The set(s) of partitions may be wells within 96 well plates. In some embodiments, the second set of partitions are wells in a second 96 well plate that each include a ligation duplex that hybridizes to an end of the initial oligos. In fact, either set of partitions may independently be provided by droplets of an emulsion, droplets in a microfluidic device, or wells of one or more multiwell plates The splitting and pooling steps may involve, for example, emulsifying into pre-templated instant partitions (PIPs) within wells of a plate, such that the set of partitions comprise wells in a multi-well plate and the second set of partitions comprise droplets of an emulsion and the splitting step comprises forming the emulsion in the wells. Thus the set of partitions and the second set of partitions may each independently be provided in any form such as droplets of an emulsion (PIPs) or wells in one or more multi-well plates.

The tripartite oligonucleotides may also include any number or any combination of an amplification primer binding site; a restriction enzyme recognition site; a G/C clamp; a unique molecular identifier; and a priming sequences that hybridizes to RNA.

In certain embodiments, the initial oligos are linked to beads and the beads include one or more of the initial oligos. The tripartite oligonucleotides may be at least about 50 to about 1000 bases in length. Preferably the length (e.g., 50, 100, 1,000, etc. bases) of the tripartite oligonucleotides have been synthesized without polymerase. Each ligating step may include annealing from about 4 to about 8 bases of a single strand of a barcode. The tripartite oligonucleotides may have a barcode space from about a few thousand (e.g., 4,000) to about several million (e.g., 7 million) to about a few hundred million (e.g., about 200 million). The method may include emulsifying the tripartite oligonucleotides with single cells in partitions and labeling cells, and molecules from the cells, with combinations of the first and second barcodes. The method may include prior to the emulsifying step, additional rounds of splitting and pooling to extend the tripartite oligonucleotides into multi-part oligonucleotides that each include at least a third barcode and optionally a fourth or more than a fourth barcode. These methods are useful for single cell sequencing (scSeq) methods such as single cell RNA sequencing (scRNASeq) methods, whereby cells may be isolated in partitions in which capture oligos are all barcoded by partitions and in which each every capture oligo further includes a unique molecular identifier (UMI) so that library preparation yields library members in which amplicons contain barcodes specific for each input molecule, and barcode specific for each "partition" (or cell that was isolated in a partition), by virtue of combinations of the first, second, and any further barcodes from the tri- or multi-partite oligonucleotide capture reagents.

BRIEF DESCRIPTION OF THE DRAWINGS

FIG. 1 presents a table of configurations that lead to 7M barcode space.

FIG. 5 depicts the anatomy of the full barcode adaptor construct.

FIG. 7 shows a tripartite oligonucleotide.

FIG. 8 shows a product with modular capture moieties.

FIG. 24 shows components of a library member.

DETAILED DESCRIPTION

Figure 2:
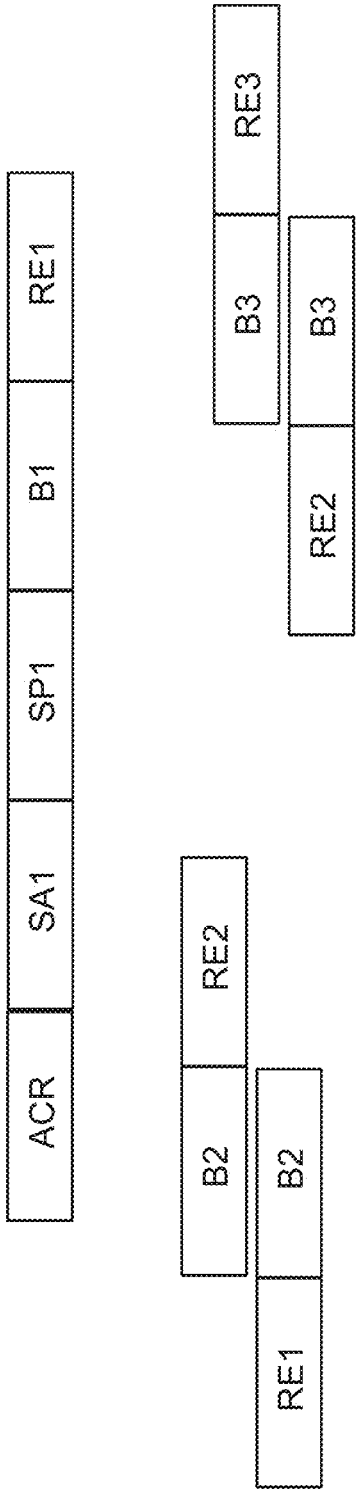
FIG. 2 shows the components for use in a 4 tier process.

The present disclosure employs multiple tiers of ligation instead of polymerization to link barcoded primers on the hydrogel. These approaches eliminate barcode error due to mis-polymerization. The disclosed methods require minimal manipulation between steps, and are faster and more economical than polymerase methods. Methods of the disclosure may include 3 or more sequential reactions, and can therefore achieve many more combinatorial barcodes while maintaining excellent separability of barcodes.

The template particles provide for the near-instantaneous self-assembly of individual targets (e.g., cells or molecules) into thousand to millions of uniform partitions. Methods of the disclosure provide extremely sensitive and unbiased preparation of nucleic acids for DNA and RNA sequencing as well as unlocking the vast potential of single cell molecular analysis, all without complex instrumentation or microfluidic consumables.

Because methods of the disclosure are useful for isolating large numbers of cells into partitions, and then preparing libraries of large numbers of molecules in each partition, the potential number of target molecules that should be tracked through an assay can potentially grow exponentially. Methods of the disclosure include reliable methods for creating very large numbers of "barcodes" for use on template particles useful to create pre-templated instant partitions ("PIPs). For example, at least certain embodiments provide template particles with a barcode space of at least about 7 million.

The high amount of barcode space avoids collisions. To avoid collisions, ligated barcodes of the disclosure may include a barcode space of 7 million. The present disclosure provides an efficient primer matrix design to achieve that goal. It may be found that ligation is preferable to primer extension or base by base synthesis. Methods of the disclosure provide resolvable barcodes with a high hamming distance. Barcodes may be made with minimized cost and minimized manufacturing effort.

Barcode collisions arise when two cells are separately encapsulated with beads that contain identical barcodes. For N assayed cells and M barcodes, the barcode collision rate is the expected proportion of assayed cells that did not receive a unique barcode:

$$1-(E(\text{cells with a unique barcode}))/\text{number of cells}.$$

Barcode collisions lead to synthetic doublets. Avoiding synthetic doublets requires high relative barcode diversity, i.e., a small ratio of N/M. It may be preferable to use 1:100 or better barcodes per cells to get below 1% collision rate.

Preferred embodiments use linker primer indexing with 7 or more batches of templates pooled together, which materials work with the existing primer extension 384×384 chemistry. For background, see "Barcode Doublets" entry dated Dec. 14, 2017, on the JEFworks web site, incorporated by reference.

FIG. 1 presents a table of configurations that lead to 7M barcode space. Different combinations from the table may be chosen to generate different scale libraries to meet multiple applications. Most embodiments will begin with a plurality of template particles (e.g., for forming PIPs) that are each pre-indexed with a first "tier" of some number of unique "linker barcodes". The template particles are split into wells of a plate and incubated with a second "tier" of barcodes, the result is pooled and then split into wells again for another tier. If three rounds of splitting into 96 well plates are performed to ligate additional tiers of barcodes to the first tier of linker barcodes, then a 4 tier barcoding process is provided.

For an initial 2 template particles, splitting by 96 to add a first tier, followed by a second 96 split tier, and a third, yields 1.7×10^6 barcode space. A barcode collision rate is kept beneath 0.2% when used with up to 3.5 million input cells.

To get to large cell capture in individual libraries, simple to pool multiple indexed PIPs in the 96×96×96 fabrication cycle.

To achieve smaller libraries, keep the same manufacturing process, but subsection the 3 tier ligation plates—this allows for optimization of a single manufacturing process, rather than maintaining multiple reagent sets and protocols for each desired library scale.

FIG. 2 shows the components for use in a 4 tier process. The components include a linker primer with an acrydite moiety for linking to a hydrogel PIP. A 3' end of the linker primer may include a first sequencing adaptor (SA1), a first sequencing site (SP1), a barcode 1 site (B1), and a first restriction site (RE1). The components also include first, second, and third ligation duplexes. The first duplex includes the RE1 site, a second barcode (B2), and a second restriction site (RE2). The second ligation duplex includes the RE2, a third barcode (B3), and a third restriction site (RE3). The third ligation duplex includes the RE2, a fourth barcode (B4), a unique molecular identifier (UMI), and any optional handle such as an adaptor, priming binding site, or primer, here shown as a poly T primer. The SA1 may be a sequencing adaptor such as an Illumina P5 olio. The SP1 may be a binding site such as an Illumina PE1 sequence.

Figure 3:
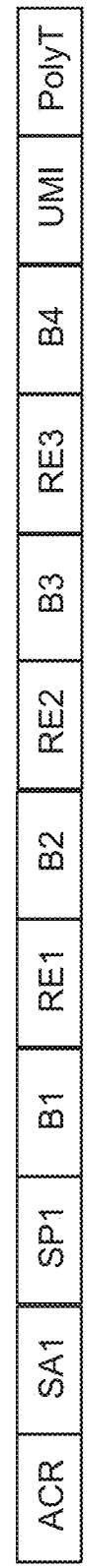
FIG. 3 shows the complete construct made by the 4 tier process.

FIG. 3 shows the complete construct made by the 4 tier process, from the 5' acrydite end to the 3' poly-T end. The total construct length may be, e.g., about 139 bases in length. Preferably, the sequence between SP1 and poly t is about 59 bases. In certain embodiments, there are about 50 bases between SP1 and poly-T. One may include shorter linker regions for ligation synthesis to allow for 2 additional barcode tiers with minimal waste sequence.

Embodiments of the ligation duplexes include restriction enzyme sites (e.g., RE1, RE2, RE3, RE4, etc.). It may be preferable to use known restriction enzymes/restriction sites as template for engineered sticky ends. The RE site can be used for diagnostics and process optimization later. Certain embodiments use one or more type II RE, preferably with one or more of (i) 4 base overlap; (ii) 3' cut bias; (iii) no cross reactivity; and (iv) 6 base recognition sequences. It may be preferable to use a common reaction buffer.

Restriction enzymes may be obtained and selected from a supplier, e.g., as listed in a catalog from a provider such as New England Biolabs. Exemplary Type II enzymes (and their recognition sequences) include: Bmtl (GCTAG/C); Kpnl (GGTAC/C); (Nsil (ATGCA/T); Pstl (CTGCA/G); Sacl (GAGCT/C); and XhoI (C/TCGAG). All listed Res have 100% cutsmart activity. It may be preferable to use different sticky end for each ligation step to prevent concatemers and non-intended primer construction.

The disclosure provides guidance for barcode unit design. For complete 7M unit barcode space, it may be preferable to use 8 linker primer barcodes (e.g., each one of the thousand to millions or more of the template particles or PIPs is linked to a plurality of copies of one linker barcode, where there are 8 different linker barcodes total). When using 3 96 well barcode plates, methods may provide 296 total barcodes, with a total barcode length of about 20-24 bases. With 6-base (i.e., 6-mer) barcodes, the unique identifier and RE sites bring the construct length up to about 48 bases (with 5-base barcodes, length goes to about 44 bases). 5 base blocks (5-mer barcodes) provides 1024 combinations. 6 base barcode blocks (6-mer) provides 4096 combinations. It may be preferable to exclude >3 identical bases in a row, aka., certain homopolymer runs. It may be preferable to establish a 2 base difference between similar bases. It may be preferable to NOT recycle barcodes across sequence blocks, i.e., to help debug mis assembly any error. Such considerations provide for robust barcodes in combinatorial barcoding.

Methods of certain embodiments include the use of a barcode-set design and decode tool, such as the tool available under the name NXCODE. See Lyons, 2017, Large-scale DNA barcode library generation for biomolecule identification in high-throughput screens, Sci Rep 7:13899, incorporated by reference. Such tools aid in the design of sets of barcodes, and then decode results from experiments incorporating these barcodes. Such tools provide barcode segregation that increases ability for accurate decoding and identification. Such tools may check for sequencing vs barcode assembly error possible. Using such tools and this disclosure, it may be preferable to provide a barcode set in which the entire set has 3 edit distance minimum across all elements; to remove elements matching RE sites; to randomize elements to increase edit distance average for barcodes in a single primer plate; and/or to sort the barcodes to maximize edit distance on each plate. Using "tiers" of barcodes provides opportunities. For example, the linker primer may be used for an assay type ID. The number of tiers may be selected based on the number of cells. For 500 cells, one may include only BC1. One may use BC2 through 9 for up to 10 k cells, etc.

In preferred embodiments, 3 "tiers", i.e., 3 96 well plates are used for ligation barcodes. Subsets may be used to tailor BC space. Elements (e.g., 93 elements) may be reserved (e.g., for negative controls). It may be desirable to retain 96 barcodes for a custom index primer set, which would leave 21 barcodes in the linker primer reserve.

Methods of the disclosure may employ a minimized primer design. Sequences of oligos may be sequentially ligated together to provide a full ligated sequence. Preferably, the full ligated sequence includes a linker (e.g., 5' acrylamide linker) followed by the full sequence.

The full barcode sequence including ligation sticky ends may be, for example, about 48 bases. The 5' sequence may be identical to any that are used in existing implementations, so that the barcoded template particles are compatible with existing single-cell sequencing (SC-Seq) protocols. Preferably, each ligation primer is 14 bp with 5' phosphorylation. Each ligation adaptor may be 14 bases with no modification.

A primer/adaptor complement analysis was performed and it was found that all disclosed embodiments had minimal off-target complementarity with favorable heat of reaction of melting, forming minimal unwanted dimers or hairpins.

The disclosed oligos may be synthesized on an oligonucleotide synthesis instrument or ordered from a commercial provider such as Integrated DNA Technologies. It may be preferable to order premixed primer/linker pairs. Linker pairs should be pre annealed before adding to sample, but will may need to be done before addition.

Other embodiments are within the scope of the disclosure.

Figure 4:
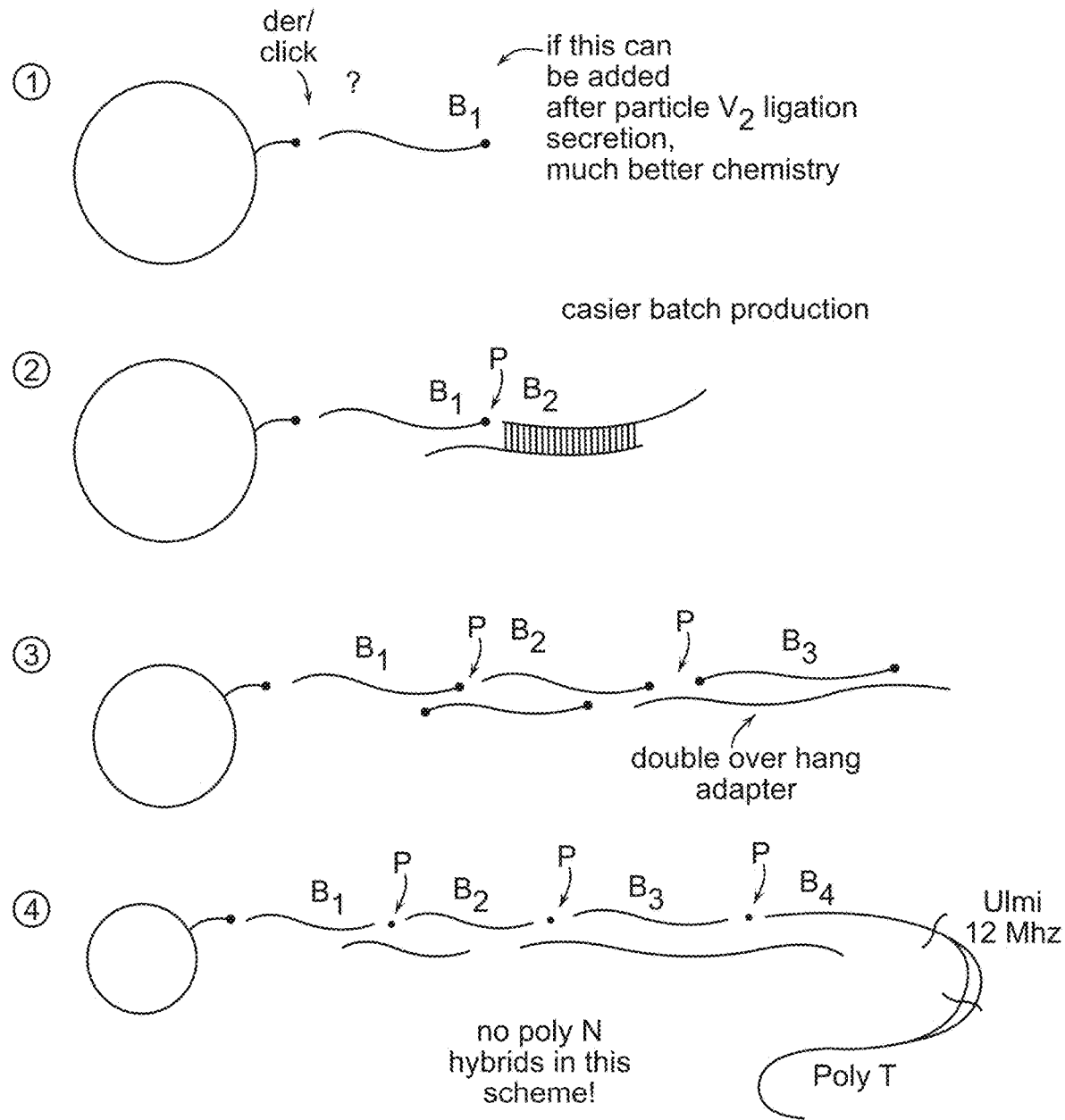
FIG. 4 shows a method for providing ligation barcodes.

FIG. 4 shows an approach to a method for provided ligation barcodes. The template particles (aka PIPs) may be linked to a linker primer (e.g., via an acrydite linkage, click chemistry, or other), aka an "initial oligo". At step 1, the first barcode (B1) is ligated to the initial oligo to form a ligation product. The B1 may be attached (e.g. ligated) to the (e.g., hydrogel) bead as a part of the oligo that includes the linker primer. Preferably, the B1 is added after the initial linker primer is attached to the bead. For example, the initial primer may be attached to the template particle (e.g., hydrogel bead) by an acrydite chemistry linkage or by click chemistry. Then, the B1 is subsequently ligated to the linker primer to form a ligation product. This approach (adding the first barcode B1 after the linker primer is attached to bead) creates favorable chemistry conditions for forming the acrydite or click chemistry linkage, which leads to easier batch production. Steps are performed in numerous partitions in parallel, with product pooled and split into partitions between steps.

For step 2, the pooled ligation products are split into a second set of partitions. A partition-specific second barcode (B2) is ligated to ligation product that includes B1 (by introducing a ligation duplex and ligase). This creates the tripartite oligonucleotide that is shown in step 2 of FIG. 4. The depicted tripartite oligonucleotide includes (i) an initial oligo, (ii) a first barcode B1, and (iii) a second barcode B2. Step 3 ligation after pooling and splitting the tripartite oligonucleotides into partitions. Step 3 shows ligating partition-specific third barcodes B3 to the tripartite oligonucleotides.

At step 3, B3 is ligated to B2. At each step transition, all wells may be pooled and then split into e.g., 96 wells for the next step. Significantly, the depicted method builds long oligonucleotide reagents on bead without polymerase-based synthesis. The long oligonucleotide reagent is built up on the particle (or bead) wholly with ligation reactions. In the depicted embodiment, B3 has a double overhang (e.g., two overhangs on the same strand), but it is noted that any number of ligation duplexes may be added before this depicted step. Then, at step 4, an oligo containing a fourth barcode (B4) is ligated to B3. The depicted oligo includes B4, a 12-mer unique molecular identifier (UMI), and a poly-T primer site. The ligations preferable use about a 5-base overhang at various steps to support short (1 hr) ligation. A 12-mer UMI is useful for deep gene counting (e.g., for uniquely tagging on the order of 4^12 unique molecules in each aqueous partition). The double overhang B3 adaptor eliminates risk of polyV mispriming.

Any disclosed element of the barcodes or adaptors may include a G/C clamp for favorable primer annealing. For example, G/C clamps to increase primer pair anneal temp may be provided in the form of bases added to flank 8 bp barcode to increase anneal temp. A simple rule is to add C if flanking base is G; otherwise add G. This results in stable primer pairs at room temperature. This also limits potential poly G or Poly C runs with barcode sequences without clamps. This also helps compensate where otherwise low GC barcodes will melt and may compromise ligation. Numerous combinations were modeled or tested and it was found that G/C clamps helpfully increased melting T, giving stability (e.g., at room T).

FIG. 5 depicts the anatomy of the full barcode adaptor construct, and shows names of, or codes for, the components. The full barcode includes a linker (to the bead), a PCR primer binding site ("PCRsite"), a first sequencer primer binding site (SP1), a first barcode, a first restriction site RE1 (e.g., Bmtl site), a G/C clamp, a second barcode, a second clamp, a second restriction site RE2 (e.g., an NsiI RE site), another clamp, a third barcode, another clamp, a third restriction site RE3 (e.g., an XhoI RE site), a fourth barcode, a unique molecular identifier (UMI), a poly-T primer, and at least one non-T base (e.g., "V", the IUPAC code for A, C, or G).

In the depicted embodiment, the total length is 141 bases and the length of the barcodes is 66 bases.

Figure 6:
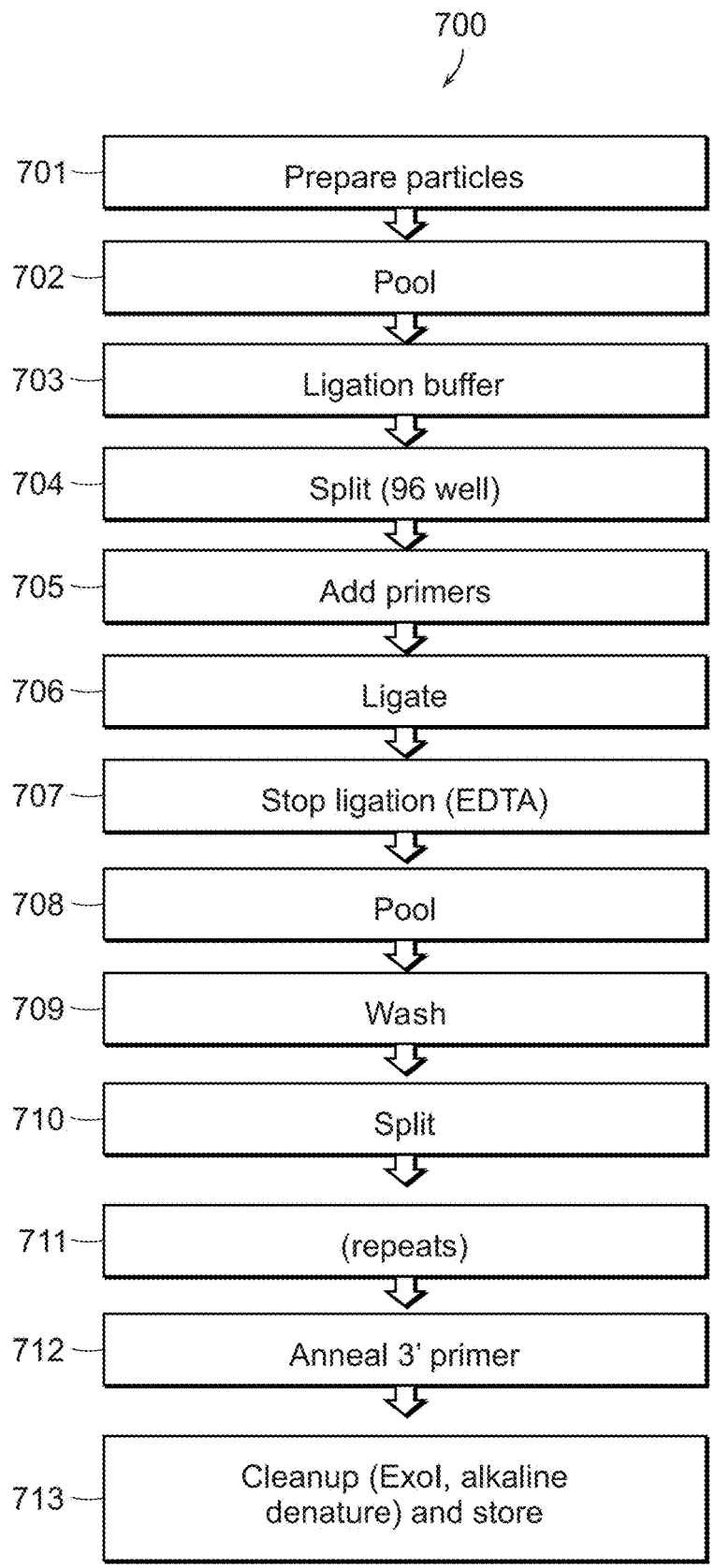
FIG. 6 diagrams a ligation protocol.

FIG. 6 diagrams a ligation protocol, or method 700 to prepare barcodes of the disclosure. The barcodes serve as target capture reagents. The method includes the following steps: Prepare 701 multiple batches of linker PIPs Preferably each linker has different barcoded linker primer (8 batches are preferable for a 7M barcode set), or "initial oligo". The initial oligo may be linked to a bead (as the PIP), which may be a hydrogel particle. The batches are pooled 702 together with matched volumes of templates. The buffer is exchanged 703 to ligation buffer. Ligase may be included in the buffer exchange 703 step. The template is divided, or "split" 704, into a set of partitions such as wells of a 96 well deep-well plate. Paired primers are added 705 from 96 well plate #1. A ligation reaction is conducted to ligate 706 the first tier, aka "first barcodes" to the initial oligos, which may preferably be linkers on the PIPs (preferably at low temp, e.g., about 10 degrees C. or even 4; incubation may be long, e.g., overnight). Ligating the first barcodes to the initial oligos create ligation products. In the described embodiments, the partitions are exemplified using wells of multi-well plates, but the described steps could be performed using microfluidics or monodisperse pre-templated instant partitions (PIPs).

The ligation reaction may be stopped 707 with EDTA. The ligation products are pooled 708. Any remaining free primer is washed 709 away. The ligation products are split 710 into a second set of partitions, such as wells of a fresh 96 well plate. Partitions-specific second barcodes are ligated to the ligation products to form tripartite oligonucleotides. These tripartite oligonucleotides each include (i) one of the initial oligos, (ii) one of the first barcodes, and (iii) one of the second barcodes. If the initial oligo includes a barcode itself, the tripartite oligonucleotides includes three distinct barcode segments.

Different combinations of steps may be repeated 711 for different products. Preferably, the method 700 includes repeat steps 705 through 710 with primer plate 2 and repeating steps 705 through 708 with primer plate 3. The wash 709 step preferably includes an alkaline denature to remove the ligation adaptor primers. A primer may be annealed 712, such as a BA19 primer to form a duplex at a 3' terminus of the complete primers. For cleanup 713, it may be preferable to do any of: alkaline denature to remove the ligation adaptor primers; anneal BA19 primer to form duplex at 3' terminus of the complete primers; ExoI digest to chew back any incomplete primer synthesis lacking poly T terminus; alkaline denature to remove BA19, and finally store. For example, one may exchange particles to storage buffer. It is noted that 8 5 ml particle batches pooled should be able to be accommodated in a single deep well plate prep (40 ml total volume–800 10 k cell reactions at 50 ul volume).

The success of the tiered ligation reactions may be demonstrated by known assays such as sequencing for fluorescence. For example, a fluorescent label may be included on, or annealed to, a 3' terminus of the barcodes and successful creation is shown by green fluorescence of the particles under microscopy. Internal results show good success for at least 4 bases of overhang at the ligation steps, which may be accomplished using sticky ends provided by, e.g., known restriction endonucleases such as those referenced above. Full 3 tier assembly has been validated by fluorescence. All that was needed was about an hour at room T for each ligation; no alkaline denaturation was required between assembly. Final cleanup included alkaline denaturation, BA19 protection, ExoI digestion, alkaline denaturation and storage. With that approach, fluorescent annealing assay validated successful assembly of a 3-tier version via method 700.

Different features may be included in the oligos to be used as capture moieties. The disclosure includes various embodiments of capture moieties for improved mRNA capture. For example, Poly T can be extended, typically for high temp applications. Certain preferred embodiments use between 20 and 40 T, e.g., 25 to 25 T, e.g., about 30 T. An LNA poly T 12mer may be used for high efficiency binding. A 7-methyl guanosine cap may be included e.g., to help with small poly A tail samples. Oligos of the disclosure may be combined with random hexamers.

Methods of the disclosure may be useful for replicating a 384×384 design but using ligation. Preferred embodiments use barcode-specific ligation adaptors, and closely replicates a 96×96×96 method. The numbers, such as 96 or 384 are exemplary and one may vary those numbers without deviating from the scope of the disclosure. E.g., one may skip a row and use 88 wells in a plate, or cross-combine plates (384×96 or 88×384×96), or use other combinations. A first embodiment uses an acrydite linker with a truncated PI sequence, where LI spans the entire sequence and is pre-ligated to the P2 primer. A second embodiment uses a PI primer, but with LI pre-ligated to templates before P2 ligation. A third version of these embodiments implements barcode specific linkers.

FIG. 7 shows a tripartite oligonucleotide comprising (i) an initial oligo, (ii) a first partition-specific barcode, and (iii) a second partition-specific barcode. The diagram shows a product of a 96×96 method with optimized ligation design. As shown, the product includes [T_linker][PCRsite] [SP1] [clamp] [barcode1] [clamp] [RE1][barcode2][UMI][PolyT]. While different approaches are possible, in the depicted embodiment, the initial oligo is [T_linker][PCRsite] [SP1], the second boarcode is [clamp] [barcode1] and the third barcode is [clamp] [RE1][barcode2][UMI][PolyT]. The full sequence may terminate with any base not T, "V". The barcode length is 36 and annealing temperature modeling shows favorable results with minimal potential for unwanted primers or hairpins.

FIG. 8 shows a product of a 96×96 method with optimized ligation design and modular capture moieties. The product shown includes [T_linker][PCRsite] [SP1] [clamp] [barcode1] [clamp] [RE1] [barcode2][UMI][RE2] followed by optionally one of [PolyT], [PolyN], [crisper feature], or [antibody tag]. The sequence may include poly T module for the capture moiety (for capturing the poly A tail of mRNA). The other capture moieties may preferably be used or added in combination with PolyT. For example, the beads (e.g., template particles) may include poly T to capture mRNA and gene-specific primers (poly N) to capture genomic DNA. Or the beads may include poly T and antibodies (to capture mRNA and proteins). The use of such modules provides for multiomics and perturb seq applications. One example may be 18 T followed by at least one non-T. One example may be C[complementary sequence]NNNNNN. One embodiment may use C[antibody barcode][PCRsite]. One example may use C[Crisper feature capture moiety].

The full modular barcode methods may be applied to a 3 tier design. For example, a fully modular 3 tier design may include [T_linker][PCRsite][HinF1][SP1][Bmtl base] [clamp][barcode1] [clamp][Nsil] [clamp] [barcode2] [clamp][XhoI] [barcode3] [UMI][PolyT], with alternative modules at the 3' end. A fully modular 2 tier design may be based on [T_linker] [PCRsite] [HinF1][PE1] [Nsil base] [clamp] [barcode1] [clamp] [XhoI] [barcode2] [UM1] [PolyT] (albeit optionally with other modules at the end). Such a multi-partite oligonucleotide capture reagent may include other features such as first and or second sequencing adaptors, [SA1] and [SA2], which could be, for example, Illumina P5 and P7 sequences.

Such ligation-based barcode synthesis to provide beads (useful for forming PIPs) may be useful in sequencing. Initially a DNA stub is attached to hydrogels via an acrydite linkage, preferably with an insoluble linker. In round 1, the first ligation duplex is introduced and ligated, to add "Barcode 1" to the newly synthesized (by ligation) barcode. At each step, an RE site (e.g., Hinf1) may be included to degrade primer dimers and pair pins. In round 2, another ligation duplex is introduced and ligated to the emerging barcode. This yields a tripartite oligonucleotide useful as a target capture reagent. The set of tripartite oligonucleotides are the fully assembled barcoded primers attached to hydrogels. To be a target capture reagent for mRNA, in some embodiments, the tripartite oligonucleotide includes at or near one end a poly T sequence. The poly-T module can be replaced with any of those referenced above. The described modular design accomodates 2 and 3 tier assembly.

In 2 tier design, the total sequence length may be about 117 bases and the coding sequence length about 37 bases. In the 3 tier design, the total sequence length may be about 133 bases, and the coding sequence length about 53 bases. Those numerals are exemplary and illustrative; not limiting. Other lengths and numbers are within the scope of the disclosure.

Figures 9, 10:
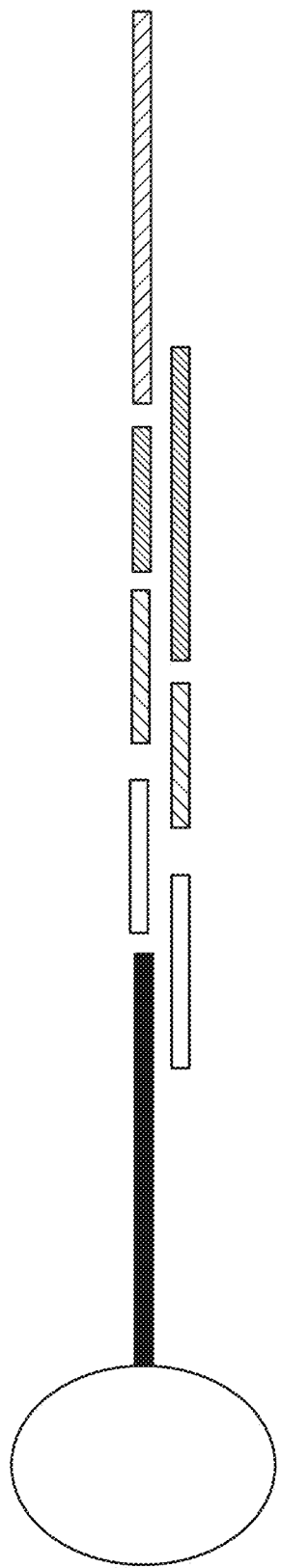
FIG. 9 diagrams parts of a 4 Tier ligation design.
FIG. 10 shows a 4 tier design.

FIG. 9 diagrams parts of a 4 Tier ligation PIPs design.

FIG. 10 lists those parts, showing [5'Acr][T-linker][SP1] B1] [L2] [B2][L3][B3] [L4] [PIPs batch barcode] [UMI] [Poly-t], where poly T may be modular and where UMI is optional and application-specific. In the depicted embodiment, the PIPs batch barcode is moved away from the hydrogel and the 5' acrydite sequence is minimized (improving ease of manufacture, because it passes off more work to ligation steps).

FIG. 10 shows the structure of a 4 tier design that includes [5'Acr] [T-linker][SP1] [B1][L2][B2][L2] [B3][L4][PIPs batch barcode][UMI][Poly-t].

Having disclosed various methods and approaching to forming multi-tier ligation-based bead oligos, in methods that use multiple tiers of ligation, one will appreciate that the disclosed bead oligos may be useful in a variety of analytical applications and research assays. For example, in some preferred embodiments, the bead oligos are used in single-cell (sc) RNA-Seq assays to, for example, profile expression levels of a plurality of mRNAs in a single cell. As each bead (aka template particle) templates the emulsification of a single cells, and ligation methods of the disclosure create multiple millions of barcodes, methods of the disclosure provide a "front end" for a high-throughput scRNA-Seq library preparation and optional sequencing assay that interrogates RNA levels across, e.g., hundreds of thousands of individual cells with high throughput.

In preferred embodiments, the beads are in an aqueous liquid and cells and other reagents are introduced (reagents, such as lysis reagents, may be delivered within the PIPs). An oil is overlaid, optionally with a surfactant (discussed in greater detail below), and the mixture is sheared or vortexed, which causes the beads to act as templates to form monodisperse emulsions, which may be referred to as pre-templated instant partitions, or PIPs. In general, a PIP comprises a template particle aka bead, a volume of partitioned fluid, and a surfactant stabilized shell or surface. Depending on the embodiments, lysis reagents may diffuse from the hydrogel beads into the aqueous partitions of the emulsion. In some embodiments, a Poly T end of the oligo hybridizes to, and captures mRNA.

After mRNA capture, reverse transcription (RT) may be performed in the PIPs or droplets of the emulsion. After mRNA capture and RT, oligos on the beads have been extended to include cDNA. The reverse transcriptase adds untemplated C bases during RT. Preferably, the oligos are attached to beads and after RT each extends to include a cDNA sequence followed by several terminal C bases. A template switching oligo (TSO) may be introduced and hybridized to the Cs. The TSO adds a common sequence to the cDNA that is used downstream for library creation. Polymerase copies the TSO thereby extending the oligos on the PIP. At this stage, oligos on the PIP terminate in the copy of the TSO and may include a preferred sequencing adaptor ("SA1"), such as the Illumina P5 adaptor. The final product may optionally include indexed sequencing adaptors and may be amplified using, for example, known platform-specific sequencing amplification primers such as Illumina forward and reverse primers.

For such an amplification, any emulsions can be freely broken and products pooled due to the barcodes introduced by the disclosed oligos. The amplification can proceed in bulk, i.e., in multiplex. This provides a pooled sequencing library where amplicons or library members are all barcoded by molecule, reaction, and cell from which they originated. The library can be stored and/or sequenced.

Sequencing yields genetic sequences that can be demultiplexed informatically by referencing the information introduced by the ligation barcodes. Embodiments of the ligated barcodes of this disclosure are useful in methods for reverse transcribing mRNA into complementary DNA (cDNA) with cells isolated within aqueous partitions. Methods of the disclosure provide for the very rapid capture of the information in mRNA into cDNA. The cDNAs are made rapidly as the sample is emulsified into droplets. Methods of the disclosure make use of particles that serve as templates for making a large number of monodisperse emulsion droplets simultaneously in a single tube or vessel. By adding cells into an aqueous mixture that includes a plurality of hydrogel template particles, layering oil over the aqueous phase, and vortexing or pipetting the tube, the particles serve as templates while the shear force of the vortexing or pipetting causes the formation of water-in-oil monodisperse droplets with on particle in each droplet. Reverse transcription reagents can be included in the initial mixture, allowing reverse transcriptase to begin simultaneously with shearing the water/oil mixture to form the emulsions. Making cDNAs from the RNAs immediately during the first stage of the droplet-making process preserves the information present as mRNA in the original cells. The disclosure provides suitable reagents and conditions for successfully reverse transcribing mRNA into cDNA while isolating a plurality of cells into monodisperse droplets in a single tube. Methods of the disclosure provide useful tools for understanding the phenotype and gene expression of a given cell at any time. In fact, the cDNA can be amplified by, e.g., polymerase chain reaction, into a plurality of stable DNA amplicons that can be stored or studied under a variety of conditions or methods. Methods of the disclosure are well-suited to making DNA libraries suitable for sequencing on a next-generation sequencing (NGS) instrument.

In certain aspects, the disclosure provides a library preparation method. The method includes preparing a mixture that includes cells and reagents for reverse transcription and vortexing or optionally pipetting the mixture. During the vortexing (or pipetting), the mixture partitions into aqueous droplets that each essentially include zero or one cell, the cells are lysed to release mRNA into the droplets, and reverse transcriptase copies the mRNA into cDNAs. The method preferably further includes amplifying the cDNAs into a library of amplicons. Preferably the mixture includes particles such that, during vortexing, the particles template the formation of the droplets. The particles may be gels that include the reagents therein. The mixture may be aqueous and the method may include adding an oil onto the mixture prior to the vortexing/pipetting. The method may include, during the vortexing, heating the mixture to a temperature that promotes activity of the reverse transcriptase (e.g., between about forty and about fifty degrees C.). The mixture is preferably sheared by any suitable mechanism or device, such as a benchtop vortexer or shaker, a pipette (e.g., micropipette), a magnetic or other stirrer or similar. The particles may be linked to capture oligos that have a free, 3' poly-T region. The particles may also include cDNA capture oligos that have 3' portions that hybridize to cDNA copies of the mRNA. The 3' portions of the cDNA capture oligos may include gene-specific sequences or oligomers. The oligomers may be random or "not-so-random" (NSR) oligomers (NSROs), such as random hexamers or NSR hexamers. The particles may be linked to capture oligos that include one or more handles such as primer binding sequences cognate to PCR primers that are used in the amplifying step or the sequences of NGS sequencing adaptors. The cDNA capture oligos may include template switching oligos (TSOs), which may include poly-G sequences that hybridize to and capture poly-C segments added during reverse transcription.

The mixture may be pre-prepared with a plurality of template particles at a number to capture a suitable target number of cells. For example, the mixture may initially include thousands, tens of thousands, hundreds of thousands, millions, or at least about 10 million template particles. Methods may be used to capture and partition any number of cells such as thousands, tens of thousands, hundreds of thousands, millions, or at least about 10 million cells.

Each of the particles may contain some of the reagents for reverse transcription. The particles may be used to template the formation of monodisperse droplets. Preferably, each of the particles serves as a template to initiate formation of aqueous monodisperse droplets in oil, in which each droplet comprises one particle. The particles may be hydrogel particles and may include, for example, polyacrylamide (PAA) or polyethylene glycol (PEG).

The disclosure provides single-tube "direct to sequencing library" methods that can be used to isolate cells into fluid partitions (e.g., droplets) while also reverse transcribing RNA into cDNA while isolating the cells into the partitions. In some embodiments, premade particles or beads, such as hydrogel particles, serve as templates that cause water-in-oil emulsion droplets to form when mixed in water with oil and vortexed or sheared. The beads are linked to tripartite oligonucleotides that each include barcodes that have been created by ligation, e.g., all of the barcode information has been provided by a first barcode and a second barcode that have been linked to an initial oligo on the bead. Those tripartite (or multi-partite, in 4-tier or higher systems) provide a target capture reagent and the template particles.

In some embodiments, an aqueous mixture is prepared in a reaction tube that includes template particles and target cells in aqueous media (e.g., water, saline, buffer, nutrient broth, etc.). An oil is added to the tube, and the tube is agitated (e.g., on a vortexer aka vortex mixer). The particles act as template in the formation of monodisperse droplets that each contain one particle in an aqueous droplet, surrounded by the oil.

The droplets all form at moment of vortexing—essentially instantly as compared to the formation of droplets by flowing two fluids through a junction on a microfluidic chip. Each droplet thus provides an aqueous partition, surrounded by oil. An important insight of the disclosure is that the particles can be provided with reagents that promote useful biological reactions in the partitions and even that reverse transcription can be initiated during the mixing process that causes the formation of the partitions around the template droplets. Moreover, the pre-templated instant partitions may be formed while the reaction mixture is being heated to a temperature that promotes activity of reverse transcriptase. In fact, data show mixing conditions and particle compositions that promote successful copying of mRNA into cDNA during mixing of the mixture to form the pre-templated instant partitions.

Methods of the disclosure are useful in making a cDNA library. A cDNA library may be a useful way to capture and preserve information from RNAs present in a sample. For example, a sample that includes one or more intact cells may be mixed with template particles to form a partition (e.g., droplet) that includes the cell. The cell can be lysed and mRNAs can be reverse transcribed into cDNAs in the droplet during the mixing stage that forms the partitions. Similarly, a sample that includes cell-free RNA can be mixed with oligo-linked template particles and mixed (e.g., shaken, vortexed, or sheared) to form droplets while simultaneously beginning the transcribe the RNA to cDNA. Whether starting with whole cells or cell-free RNA, the result is the formation of droplets that include cDNA copies of the starting RNA. Because the cDNA is more stable than RNA (e.g., cDNA does not include 2' hydroxyl groups that autocatalyze the molecule's own hydrolysis), the droplets provide a stable cDNA library that may be used in downstream assays to study the RNA content of the starting sample.

Forming the cDNAs while initially forming the droplets avoids problems caused by the ephemeral nature of mRNA. Sample preparation and library preparation methods of the disclosure improve the ability of laboratory techniques to study RNA compositions of a sample. In fact, cells can be sequestered into aqueous partitions while also, simultaneously copying the mRNAs into stable cDNA that may be stored and studied downstream.

Figure 11:
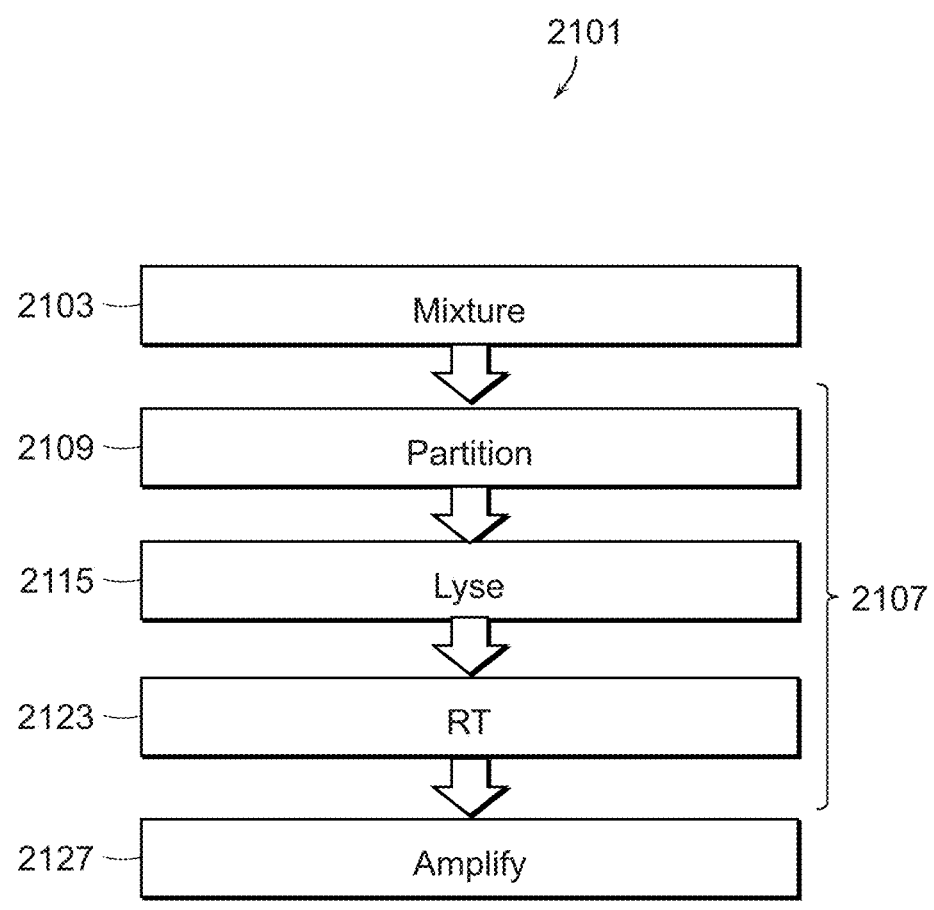
FIG. 11 diagrams a library preparation method.

FIG. 11 diagrams a library preparation method 2101. The method includes preparing 2103 a mixture that includes cells and reagents for reverse transcription. While any suitable order may be used, it may be useful to provide a tube that includes template particles. The template particles may be provided in an aqueous media (e.g., saline, nutrient broth, water) or dried to be rehydrated at time of use. A sample may be added into the tube—e.g., directly upon sample collection from a patient, or after some minimal sample prep step such as spinning whole blood down, re-suspending peripheral blood monocytes (PBMCs), and transferring the PBMCs into the tube. Preferably an oil is added to the tube (which will typically initially overlay the aqueous mixture). The method 2101 then includes vortexing 2107 or pipetting the mixture to shear the fluid causing partitioning. It may be found that during the vortexing: the mixture partitions into the aqueous droplets within about 5 to about 50 seconds, and then the cells are lysed within about 30 seconds to about a few minutes, and then the reverse transcriptase begins to copy the mRNA.

During the vortexing, several things are accomplished. The mixture partitions 2109 into aqueous droplets that each include zero or one cell. When the sample includes whole cells such as PBMCs, the cells are lysed 2115 to release mRNA into the droplets. The lysing 2115 is an optional step, as the method 2101 may be used where the original sample includes cell-free RNA. Additionally, reverse transcriptase copies 123 the mRNA into cDNAs. Lysis may be performed chemically (e.g., using micelles to deliver lysis agents), by activated chemistry (e.g., thermal, light, etc), and/or enzymatically (heat activated). A mix of micelle/chemical plus heat-activated enzymes has been tested.

Embodiments of the disclosure employ chemical lysis methods including, for example, micelle-based methods. Methods may include using micelles to deliver suitable lysis agents. Suitable lysis agents include Sarkosyl, SDS, Triton X-100. One or more surfactants is used to micellize the lysis agent into the oil phase. Suitable surfactants for creating micelles may include, for example Ran or ionic Krytox. It may be useful to use a super-concentrated co-solvent to aid dissolution of the lysis agent. Some embodiments use a combination of fluoro-phase surfactant Krytox 157-FSH (acidic form) or neutralized form (ammonium counter-ion, potassium counter-ion or sodium counter-ion) in 0.05%-5% in Novec 7500 or 7300 or 7100 or Fluorinert to form micelles that include a lysis agent such as Sarkosyl or SDS at 0.05%-5%. In certain embodiments, a fluoro-phase surfactant such as Perfluorpolyether PEG-conjugates is used with a non-ionic lysis agent such as Triton-X100 or IGEPAL at 0.05%-2%. Fluorocarbon based oil system may be used, e.g., 3M Novec HFE (e.g. HFE7000, 7100, 7200, 7300, 7500, 7800, 8200) or 3M Fluorinert (e.g. FC-40, -43, -70, -72, -770-3283. -3284). Embodiments may use surfactant for fluorocarbon-based oil, e.g., commercially available compounds such as Chemour Krytox 157FSH, Chemour Capstone etc. Ionic type fluorophase surfactants may include Perfluoroalkyl carboxylates, Perfluoroalkyl sulfonates, Perfluoroalkyl sulfates, Perfluoroalkyl phosphates, Perfluoropolyether carboxylates, Perfluoropolyether sulfonates, or Perfluoropolyether phosphates. Non-ionic type fluorophase surfactant may include Perfluoropolyether ethoxylates or Perfluoroalkyl ethoxylates. A silicone based oil system may be used such as polydimethylsiloxane (PDMS) with viscosity range between 0.5-1000 cst. Suitable surfactant for silicone based oil may be used such as Gelest Reactive Silicones, Evonik ABIL surfactant, etc. An ionic type silicone phase surfactant may be carboxylate terminated PDMS or Amine terminated PDMS. A non-ionic type silicone phase surfactant may be hydroxyl terminated PDMS or PEG/PPG functionalized PDMS. A hydrocarbon based oil system may use heavy alkane hydrocarbons with carbon atoms number greater than 9. The oil could include a single compound or a mixture from multiple compounds. For example, tetradecane, hexadecane, mineral oil with viscosity range between 3 to 1000 cst. Suitable surfactant for hydrocarbon based oil (ionic) may include Alkyl carboxylates, Alkyl sulfates, Alkyl sulfonates, Alkyl phosphates or (non-ionic) PEG-PPG copolymers (e.g. Pluronic F68, Pluronic F127, Pluronic L121, Pluronic P123), PEG-alkyl ethers (e.g. Brij L4, Brij 58, Brij C10), PEG/PPG functionalized PDMS (e.g. Evonik ABIL EM90, EM180), Sorbitan derivatives (e.g. Span-60, Span-80, etc.), or Polysorbate derivatives (e.g. Tween-20, Tween 60, Tween 80). To achieve best micellization/co-dissolution performance and minimum disruption of water-in-oil droplet interface, the general rule of thumb for lysis agent/oil phase surfactant combination is as follow: (i) an ionic type lysis agent is preferred for combination with ionic oil phase surfactant, such lysis agent may include but not limited to: SDS, Sarkosyl, sodium deoxycholate, Capstone FS-61, CTAB; (ii) a non-ionic type lysis agent is preferred for combination with non-ionic oil phase surfactant, such lysis agent may include but not limited to: Triton X-100, Triton X-114, NP-40, Tween-80, Brij 35, Octyl glucoside, octyl thioglucoside; and/or (iii) a zwitterionic type lysis agent may be used in combination with either ionic or non-ionic oil phase surfactant, such lysis agent may include but not limited to: CHAPS, CHAPSO, ASB-14, ASB-16, SB-3-10, SB-3-12.

As shown, two important phenomena are accomplished during and/or after the vortexing 2107 step: aqueous partitions form 2109 and reverse transcription 2123 occurs.

Importantly, a plurality (e.g., thousands, tens of thousands, hundreds of thousands, millions, or tens of millions or more) of aqueous partitions are formed 2109 essentially simultaneously. Results have shown that this consistently works. It may be preferable to use template particles (e.g., a corresponding number of hydrogel particles that serve as templates to the formation of droplets). Reagents may be provided to promote cell lysis or initiate reverse transcription. Once the vortexing 2107 step has been performed, at least one of the droplets will have at least one cDNA copy of an RNA from the starting sample. For background overview, see generally Gubler, 1983, A simple and very efficient method for generating cDNA libraries, Gene 25 (2-3):263-9 and Figueiredo, 2007, Cost effective method for construction of high quality cDNA libraries, Biomolecular Eng 24:419-421, both incorporated by reference. Preferably, one or a plurality of the droplets will each have a plurality of cDNAs that include droplet-specific oligonucleotide barcodes for a plurality of corresponding RNAs that were partitioned into the droplets by the partitioning 2109. Forming the cDNA(s) may include attaching amplification primer-binding sites (such as first and second universal priming sequences at the ends of the cDNAs), and the method 2101 optionally includes amplifying 2127 the cDNA(s) into amplicons, which may be stored or analyzed. For example, the amplicons may be sequenced using a sequencer such as a next-generation sequencing (NGS) instrument.

To prepare 2103 the mixture that includes cells and reagents, template particles may be provided. Template particles may be made of any suitable material such as, for example, polyacrylamide, poly (lactic-co-glycolic acid), polyethylene glycol, agarose, or other such material. In some embodiments, hydrogel particles are prepared. In some embodiments, 6.2% acrylamide (Sigma-Aldrich), 0.18% N,N'-methylene-bis-acrylamide (Sigma-Aldrich), and 0.3% ammonium persulfate (Sigma-Aldrich) are used for PAA particle generation. A total of 14% (w/v) 8-arm PEGSH (Creative PEGworks) in 100 mM NaHCO3 and PEGDA (6 kDa, Creative PEGworks) in 100 mM NaHCO$_3$ may be used for PEG particle generation. A 1% low melting temperature agarose (Sigma-Aldrich) may be used for agarose particle generation. The agarose solution is warmed to prevent solidification. Agarose and PEG solutions are injected into a droplet generation device with the oil (HFE-7500 fluorinated oil supplemented with 5% (w/w) deprotonated Krytox 157 FSH) using syringe pumps (New Era, NE-501). The PAA solution is injected into the droplet generation device with the fluorinated oil supplemented with 1% TEMED The hydrogel solution and oil are loaded into separate 1 mL syringes (BD) and injected at 300 and 500 µL, respectively, into the droplet generation device using syringe pumps. The PAA and PEG droplets are collected and incubated for 1 h at room temperature for gelation. The agarose droplets are incubated on ice for gelation. After gelation, the gelled droplets are transferred to an aqueous carrier by destabilizing them in oil with the addition of an equal volume of 20% (v/v) perfluoro-1-octanol in HFE-7500. The particles are washed twice with hexane containing 2% Span-80 (Sigma-Aldrich) to remove residual oil. Following the hexane wash, the particles are washed with sterile water until all oil is removed.

In some embodiments, the template particles are provided in some form of tube or sample vessel for steps of the method 2101. Any suitable vessel may be used. For example, a sample vessel may be an, e.g., 50 or 150 mL, microcentrifuge tube such as those sold under the trademark EPPENDORF. The sample vessel may be a blood collection tube such as the collection tube sold under the trademark VACUTAINER. The tube may be a conical centrifuge tube sold under the trademark FALCON by Corning Life Science. In preferred embodiments of the method, the template particles are provided in a tube within an aqueous media such as a buffer, nutrient broth, saline, or water.

A sample that contains RNA is obtained, to be added to the particles. Any suitable sample may be used. Suitable samples include environmental, clinical, library specimen, or other samples with known or unknown RNA present as cell-free RNA or present in tissue or cells (living or preserved) containing the RNA. Suitable samples may include whole or parts of blood, plasma, cerebrospinal fluid, saliva, tissue aspirate, microbial culture, uncultured microorganisms, swabs, or any other suitable sample, For example, in some embodiments, a blood sample is obtained (e.g., by phlebotomy) in a clinical setting. Whole blood may be used, or the blood may be spun down to isolate a component of interest from the blood, such as peripheral blood monocytes (PBMCs). The sample is then preferably added to a mixture such as the particles in the tube. For the method 2101 it is preferable that the mixture include reagents for reverse transcription such as reverse transcriptase.

Figure 12:
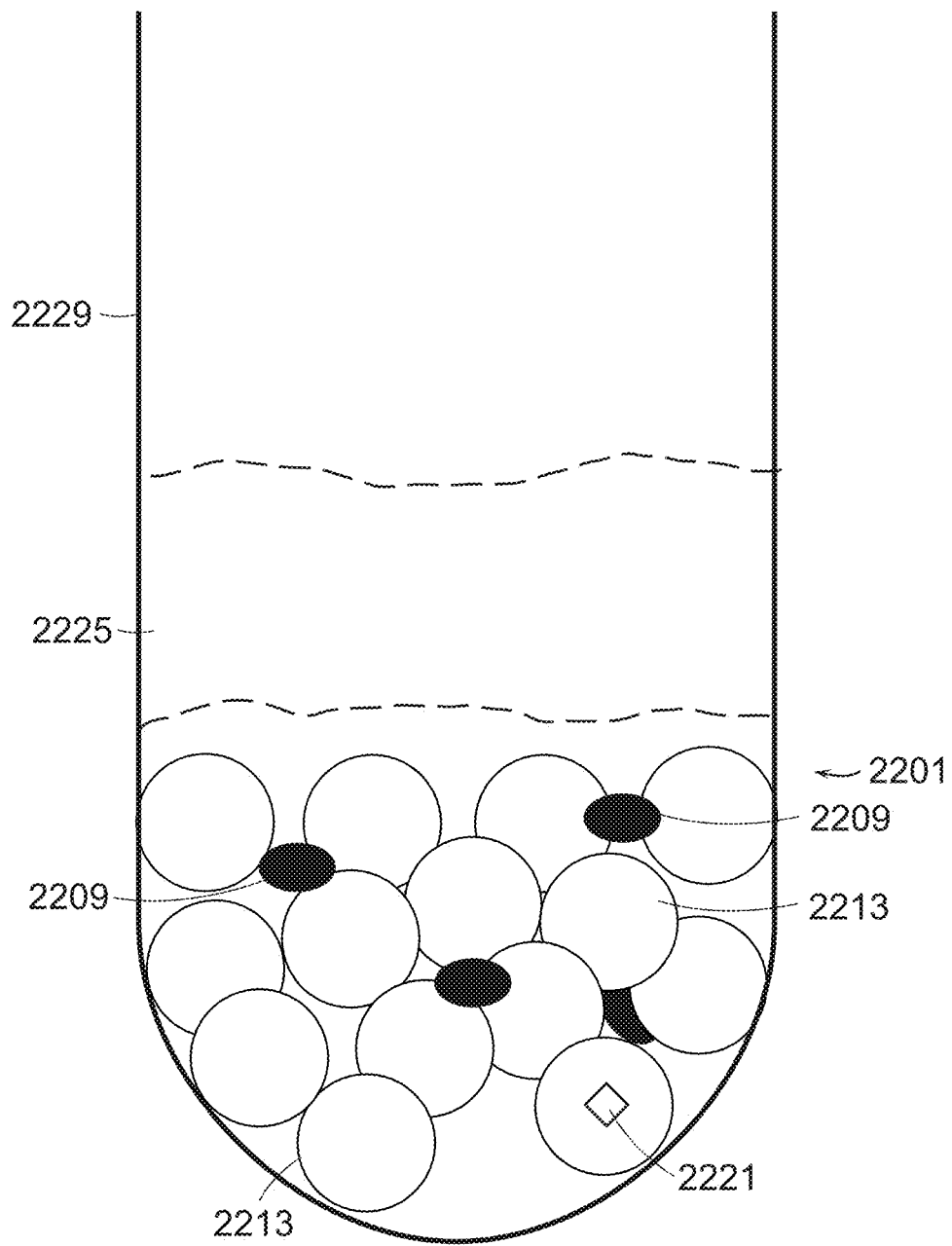
FIG. 12 shows a mixture with cells 2209 and reagents 221 for reverse transcription.

FIG. 12 shows a mixture 2201 that includes cells 2209 and reagents 221 for reverse transcription. As shown, the mixture 2201 is provided in a sample vessel 2229 or tube. The tube initially includes particles 2213 that will serve as template particles for partition formation in subsequent steps. The reagents 2221 may be provided by various methods or in various formats. In the depicted embodiments, the reagents 2221 are provided by the particles 2213. When using particles 2213 of a certain structure, such as hydrogels, the reagents 2221 may be enclosed within, embedded with, stuck to, or linked to the particles 2213. As shown, the particles 2213 and the cells 2209 sit within an aqueous mixture 2201. The method 2101 may include adding an oil 2225 onto the mixture 2201 prior to any vortexing 2107. It may be preferable to use a fluorinated oil for the oil 2225, and a surfactant such as a fluorosurfactant may also be added (separately, or with the oil 2225, or with the aqueous mixture 2201). See Hatori, 2018, Particle-templated emulsification for microfluidics-free digital biology, Anal Chem 90:9813-9820, incorporated by reference. It may be found that aqueous-soluble surfactants promote formation of monodisperse (each droplet has one particle and each particle gets a droplet) droplets. Preferred materials for the hydrogel particles 2213 include polyacrylamide (PAA) and PEG. In one preferred embodiment, the sample vessel 2229 includes comprise PAA particles 2213 with 0.5% Triton suspended in 1.25 volume of HFE oil 225 with 2% (20 µL) or 5% (200 µL and 2 mL) fluorosurfactant. Once the aqueous mixture 201 is prepared, the mixture is vortexed.

The mixture may be vortexed by any suitable method or mechanism. The mixture may be contained in a tube such as a microcentrifuge tube. The tube may be manually flicked, or pressed down on a benchtop vortexer. The mixture may be in a well in a plate, such as a 96-well plate, and the plate may be loaded onto a benchtop mixer or shaker. The mixture may be in one tube of an 8-tube strip of microcentrifuge tubes such as the 8-tube strip sold under the trademark EPPENDORF. In a preferred embodiment, the tube is loaded into a vortexing instrument.

Figure 13:
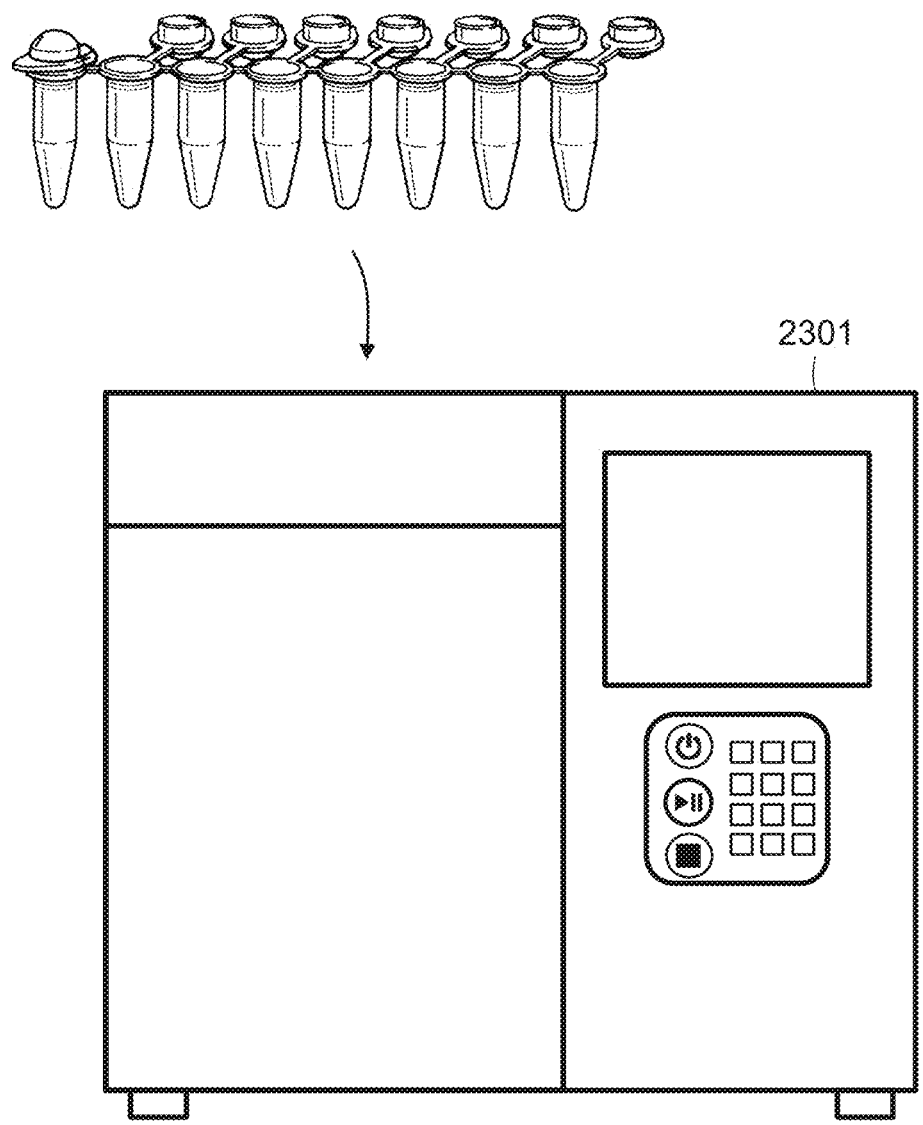
FIG. 13 shows loading an 8-tube strip into an instrument 2301 for vortexing.

FIG. 13 shows loading an 8-tube strip into an instrument 2301 for vortexing 2107 the mixture (where the reaction vessel 2229 is one of the 8 tubes in the strip). The instrument 2301 vortexes 2107 the mixture 2201. During and/or subsequent to the vortexing, two things happen: droplets are generated that contain RNA and the RNA is transcribed to cDNA. The method 2101 may include, during the vortexing 2107, heating the mixture to a temperature that promotes activity of the reverse transcriptase. For example, the instrument 2301 may include a heater that heats the sample vessel 2229. The sample vessel 2229 and/or reaction mixture 2201 may be heated to a temperature for example between about forty and about fifty degrees C. The heating and the vortexing 2107 may be performed within or on the vortexing instrument 2301. Based on data shown below, preferably the vortexing instrument 2301 vortexes the mixture 2201 at a rate between about two hundred and about seven hundred rpm, e.g., more preferably between about 400 and 600 rpm, e.g., about 500 rpm. Within the sample vessel 2229, during vortexing (or shaking, or shearing, or agitating, or mixing), each of the particles 2213 preferably contain some of the reagents 221 for reverse transcription and each of the particles 2213 serves as a template to initiate formation of aqueous monodisperse droplets in oil, in which each droplet comprises one particle 2213.

Figure 14:
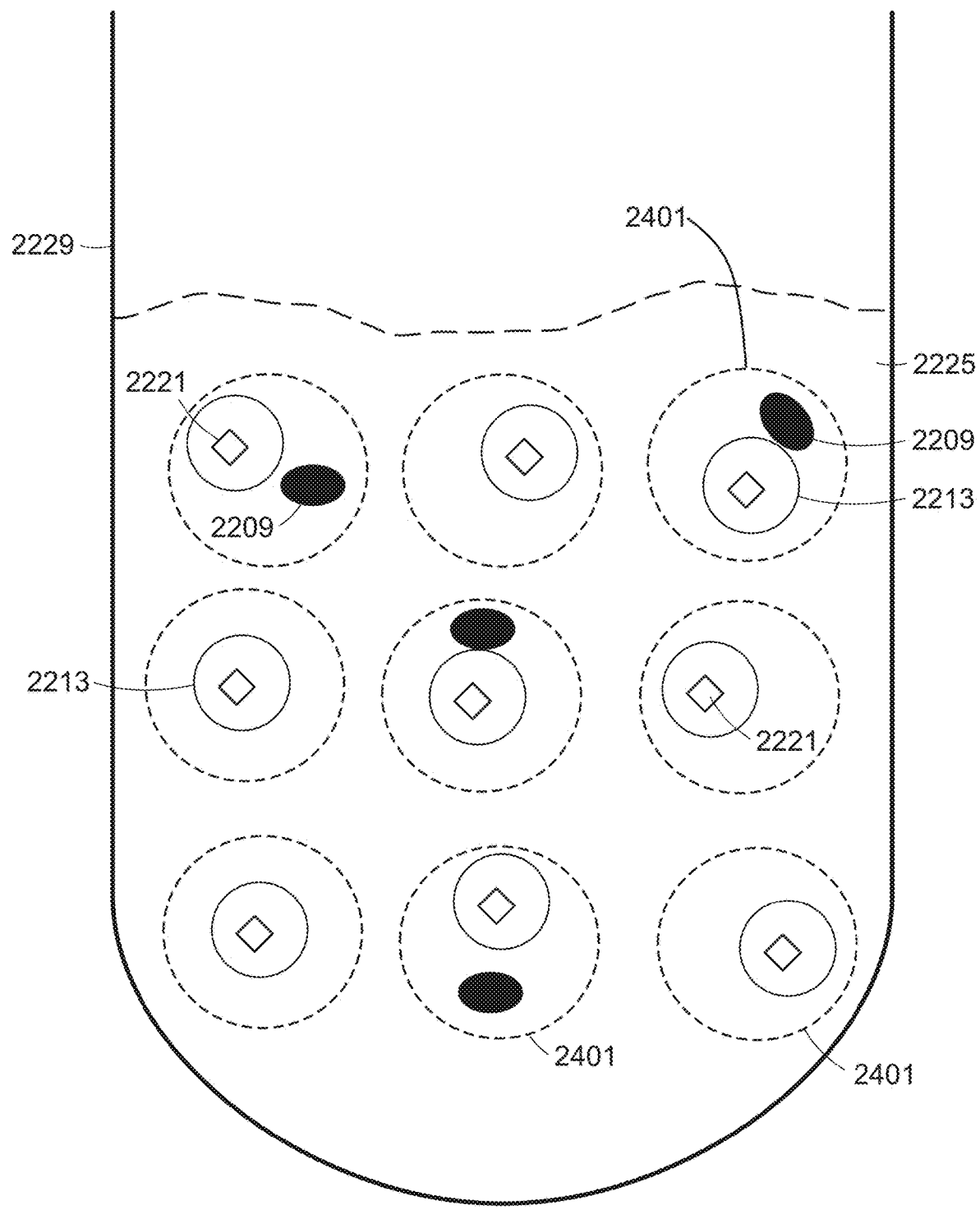
FIG. 14 shows the droplets 2401, or PIPs, formed during vortexing.

FIG. 14 shows the droplets 2401, or PIPs, formed during vortexing 2107 (a PIP is a pre-templated instant partition). During the vortexing 2107, the particles 2213 template the formation of the droplets 2401. Reverse transcription may occur or begin during or after the vortexing 2107. The particles 2213 and/or the mixture 2201 may include reagents 2221 useful for reverse transcriptions. For example, where the particles 2213 are hydrogels having reagents embedded or enclosed therein, the particles may release reagents 2221 into the droplets 2401 as the droplets form. The particles may release the reagents as a natural consequence of forming the aqueous mixture 2201 and vortexing 2107 (e.g., due to osmotic or phase changes associated with introduction of an aqueous fluid, the sample, or via salts that are introduced to influence osmotic/tonic conditions. The reagents may be released by stimulus (e.g., sonication, heat, or the vortexing 2107 itself). The reagents may migrate electrophoretically from the particles 2213 into the surrounding aqueous media under the influence of electrostatic charge (e.g., self-repulsion out of the particles). Some or all of the reagents may be provided in or with (embedded within or surface-linked to) the particles 2213 while additional or alternatively some or all of the reagents may be separately added to the sample vessel 2229.

For example, in some embodiments, certain molecular reagents such as polymerase enzymes are packaged in the particles, some reagents such as oligonucleotides are linked (e.g., covalently) to the particles, and some reagents such as lysis agents (e.g., detergent), dNTPs, and metal ions are added independently.

Figure 15:
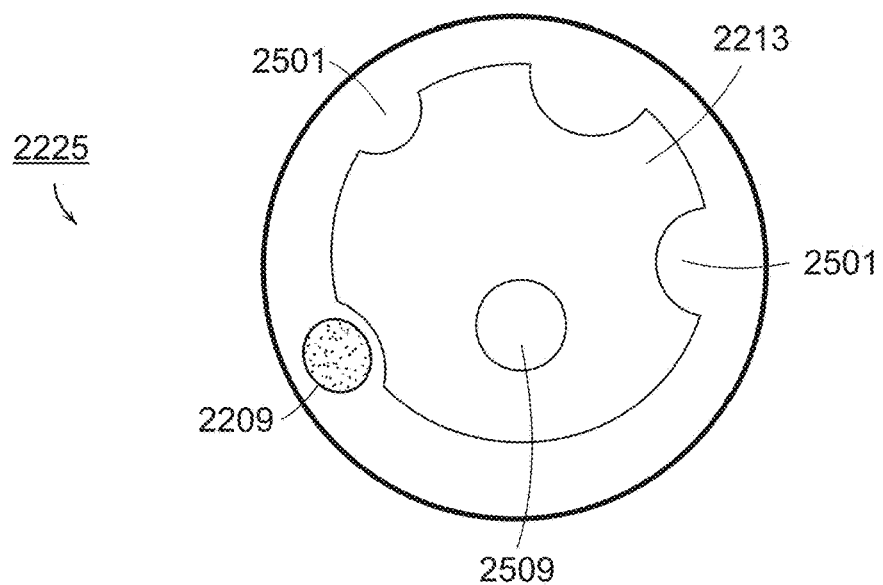
FIG. 15 is a detail view of a droplet.

FIG. 15 is a detail view of a droplet 2401 according to certain embodiments. Droplets formed according to methods of the disclosure are monodisperse meaning that the vast majority of the droplets 401 will include one particle 2213 and the vast majority of the particles 2213 will form into one droplet 2401. Said another way, monodisperse means that comparing the number of template particles 2213 initially provided in the aqueous mixture 201 to the number of droplets 2401 produced by vortexing, the smaller number will be at least 90% of the larger number, and in practice usually at least 95%, more preferably 98% or 99%. Under optimal conditions, it is 99.9%. Each particle 213 may include a number of features to promote the methods herein. For example, each particle is preferably composed of a hydrogel such as poly-acryl amide (PAA). The particles may preferably be non-spherical and instead include recesses 2505 or quasi-planar facets that tend to promote the association of cells 2209 with the particles 2213 during formation of the droplets 2401 in the tube 2229. Each particle 2215 may include one or more of an interior void space or compartment 2509 where reagents are held prior to vortexing or introduction of aqueous media. While compartments may be understood as open pockets of space having reagents therein, it may also be understood that reagents are packed into or embedded within the particles 2213. It may also be found that during formation of the particles 2213 that, due to electrostatic forces, water-soluble reagents migrate to a shell near an outer portion of the particle 2213 and readily diffuse into aqueous media when the particle 2213 is inundated therein. Other features, compositions, and morphologies are within the scope of the disclosure.

Figure 16:
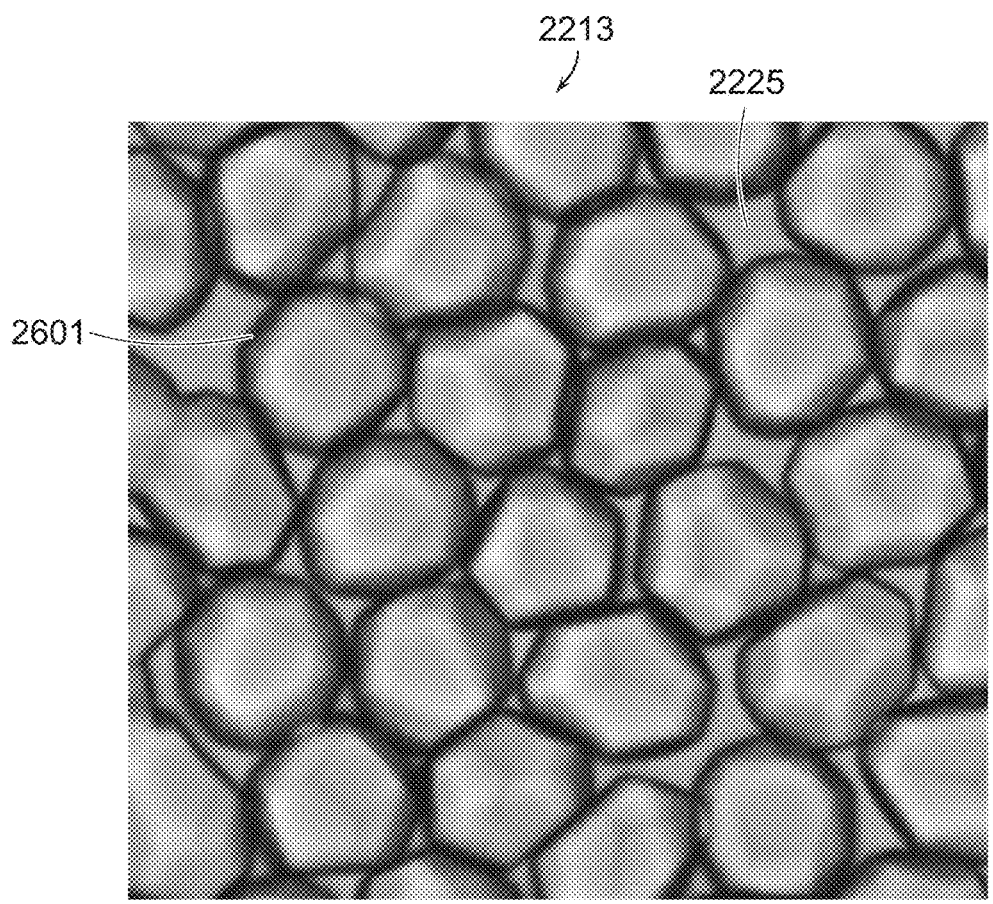
FIG. 16 is a photomicrograph showing a plurality of PAA particles.

FIG. 16 is a photomicrograph showing a plurality of PAA particles having quasi-planar facets. The depicted morphology may be preferred for sequestering cells into droplets. A benefit of hydrogel particles such as PAA is that methods exist for linking the particles to useful molecular structures such as oligonucleotide capture probes or primers. Covalent linkage can be provided via an acrylamide group and or through a disulfide linkage (which can be released in-droplet by providing reducing condition, e.g., by introducing beta mercaptoethanol or dithiothreitol).

Figure 17:
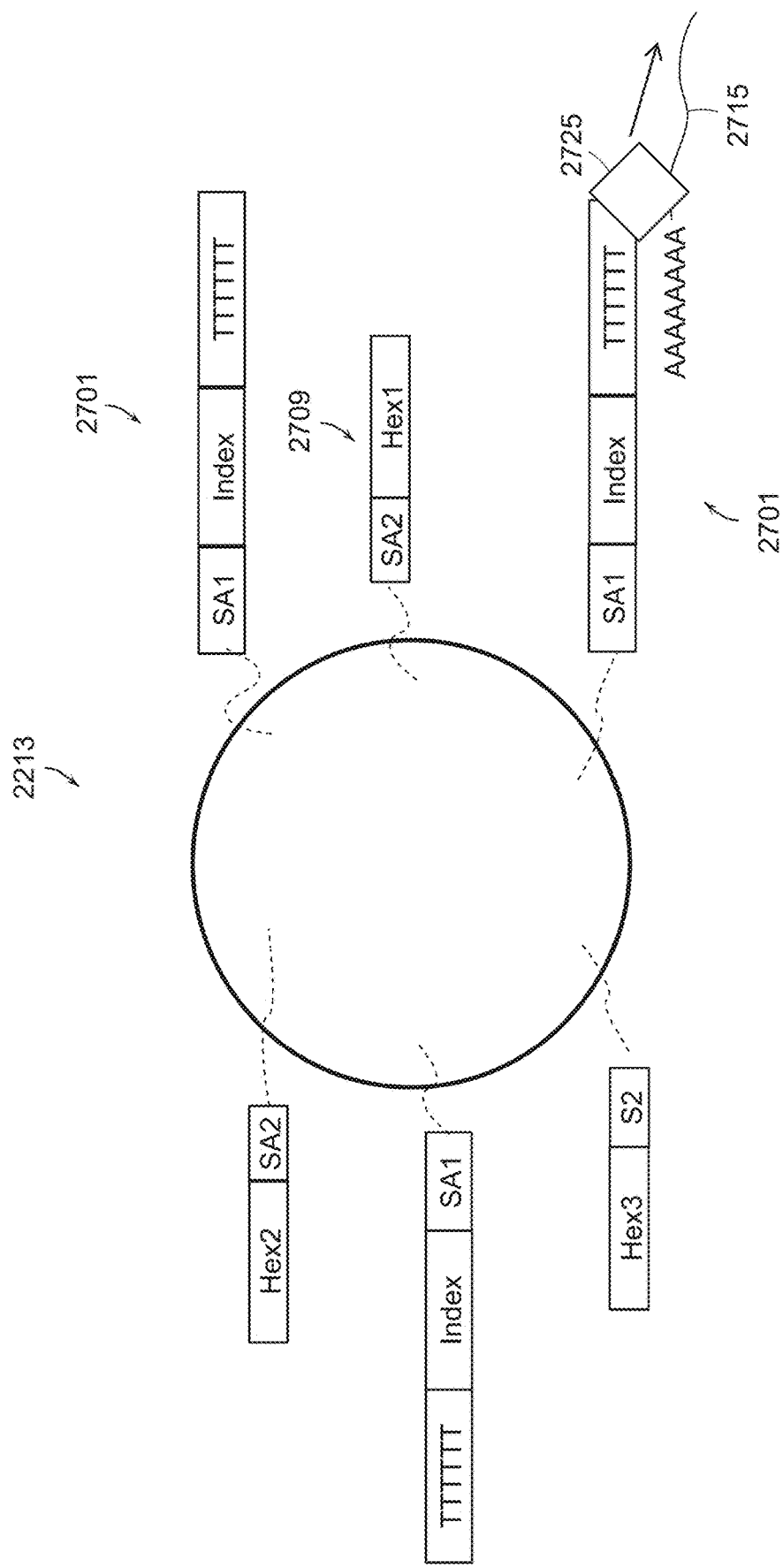
FIG. 17 shows particles aka beads linked to capture oligos.

FIG. 17 shows an embodiment in which the particles 2213 are linked to capture oligos useful for initiating reverse transcription. As shown, the particle 2213 is linked to (among other things) mRNA capture oligos 2701 that include a 3' poly-T region (although sequence-specific primers or random N-mers may be used). Where the initial sample includes cell-free RNA, the capture oligo hybridizes by Watson-Crick base-pairing to a target in the RNA and serves as a primer for reverse transcriptase, which makes a cDNA copy of the RNA. Where the initial sample includes intact cells, the same logic applies but the hybridizing and reverse transcription occurs once a cell releases RNA (e.g., by being lysed).

In preferred embodiments, the target RNAs are mRNAs. For example, methods of the disclosure may be used to make a cDNA library useful for showing an expression profile of a cell. Where the target RNAs are mRNAs, the particles may include mRNA capture oligos 701 useful to at least synthesize a first cDNA copy of an mRNA. The particles 213 may further include cDNA capture oligos 2709 with 3' portions that hybridize to cDNA copies of the mRNA. For the cDNA capture oligos, the 3' portions may include gene-specific sequences or hexamers. As shown, the mRNA capture oligos 2701 include, from 5' to 3', a binding site sequence SA1, an index, and a poly-T segment. The cDNA capture oligos include, from 5' to 3', a binding sequence SA2 and a hexamer. Any suitable sequence may be used for the SA1 and SA2 binding sequences. For example, either or both of those may be an Illumina P5 and/or P7 sequence or an arbitrary universal priming sequence (universal meaning that the sequence information is not specific to the naturally occurring genomic sequence being studied, but is instead suited to being amplified using a pair of cognate universal primers, by design). The index segment may be any suitable barcode or index such as may be useful in downstream information processing. It is contemplated that the SA1 sequences, the SA2 sequence, and the index segment may include the P5 and P7 sequences use in NGS indexed sequences such as performed on an NGS instrument sold under the trademark ILLUMINA, and as described in Bowman, 2013, Multiplexed Illumina sequencing libraries from picogram quantities of DNA, BMC Genomics 14:466 (esp. in FIG. 2 in Bowman 2013), incorporated by reference. The hexamer segments may be random hexamers or selective hexamers (aka not-so-random hexamers). The particle 2213 is depicted as including 3 hexamer segments labelled Hex1, Hex2, and Hex3, but it will be appreciated that the particle 2213 may be linked to many, e.g., thousands, of distinct hexamers. Hexamers are illustrated, but any suitable oligomers may be used. Preferred embodiments make use of not-so-random (NSR) oligomers (NSROs). See Armour, 2009, Digital transcriptome profiling using selective hexamer priming for cDNA synthesis, Nat Meth 6(9):647-650, incorporated by reference. Preferably, the particles 2213 are linked to capture oligos 2701, 2709 that include one or more primer binding sequences SA1, SA2 cognate to PCR primers that may be used in an option downstream amplifying step (such as PCR or bridge amplification).

As shown, a capture oligo 701 hybridizes to an mRNA 2715. A reverse transcriptase 2725 binds and initiates synthesis of a cDNA copy of the mRNA 2715. Note that the mRNA 2715 is connected to the particle 2213 non-covalently, by Watson-Crick base-pairing. The cDNA that is synthesized will be covalent linked to the particle 2213 by virtue of the phosphodiester bonds formed by the reverse transcriptase 2725.

Figure 18:
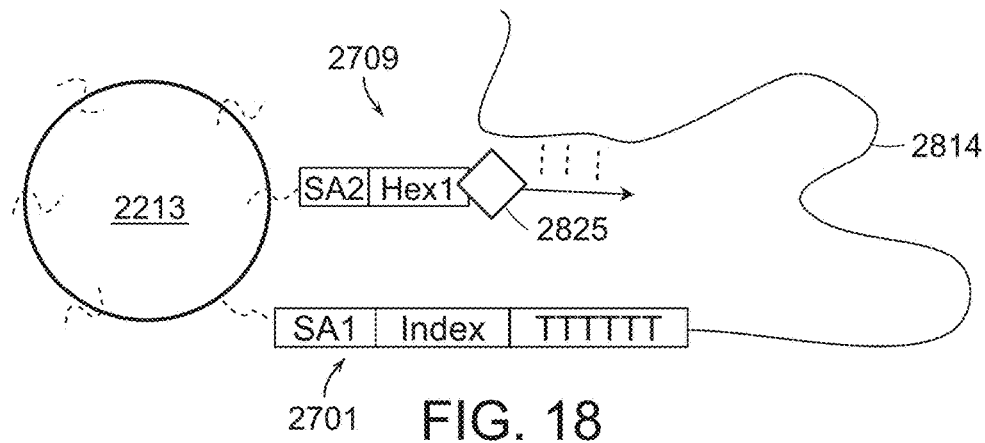
FIG. 18 shows a cDNA.

FIG. 18 shows a cDNA 2814 linked to a particle by virtue of its being a covalent, polymeric extension of the mRNA capture oligo 2701. As shown, a 3' end of the cDNA capture oligo 2709 will hybridize to the cDNA 814. A polymerase will perform second-strand synthesis, copying the cDNA by extending the cDNA capture oligo 2709.

Figure 19:
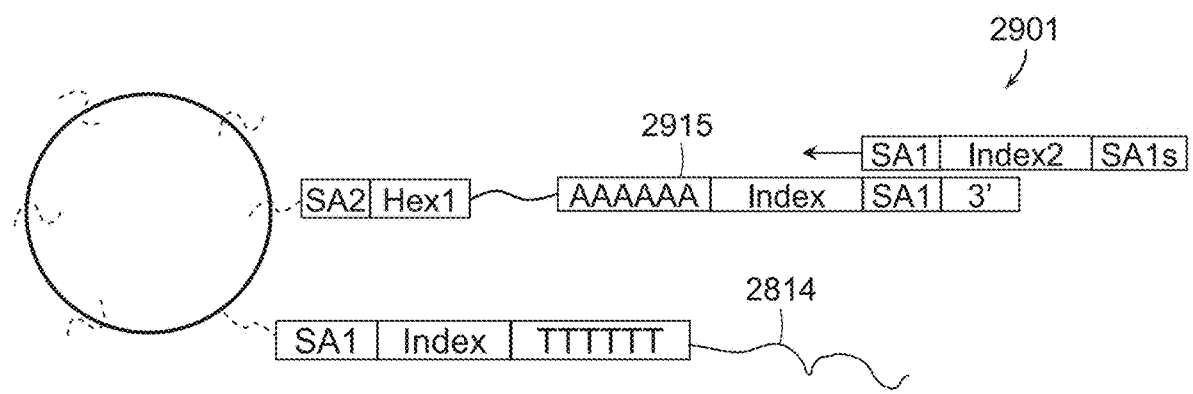
FIG. 19 shows a first sense copy of a cDNA.

FIG. 19 shows a first sense copy 2915 of the cDNA 2814. The first sense copy 2915 is in the same sense as the mRNA 2715, both of which are antisense to the cDNA 2814. At this stage, RNaseH may be introduced to degrade the mRNA 2715. A free forward primer 2901 is introduced that will hybridize to, and prime copying of, the first sense copy 2915 of the cDNA 2814.

Figure 20:
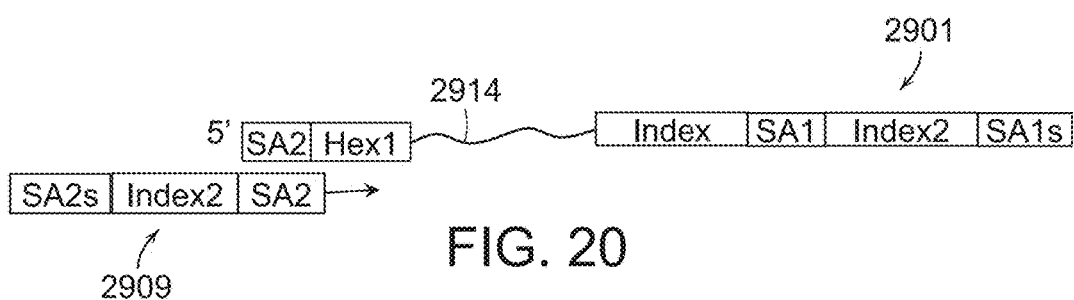
FIG. 20 shows the antisense copy of an mRNA.

FIG. 20 shows the antisense copy 2914 that is made by extending the free forward primer 2901. A free reverse primer 2909 is introduced that hybridizes to the antisense copy 2914. As shown, the free forward primer 2901 and the free reverse primer 2909 each have respective handles SA1 and SA2. Those handles SA1, SA2 (e.g., Sequencing Adaptor 1, Sequencing Adaptor 2) may be any arbitrary sequence useful in downstream analysis. SA1 and SA2 may be, for example, Illumina P5 and P7 sequences. For example, they may be additional universal primer binding sites or sequencing adaptors. The free reverse primer 2909 primers a polymerase-based synthesis of a sense copy 2915 of the original mRNA 2715.

Figure 21:
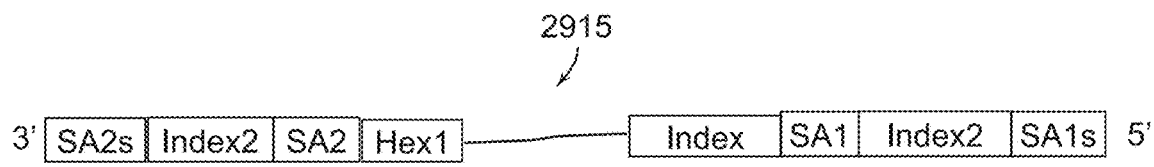
FIG. 21 shows a sense copy of an mRNA.

FIG. 21 shows the sense copy 2915 of the original mRNA 2715. It may be appreciated that the free forward primer 2901, the free reverse primer 2909, the antisense copy 2914, and the sense copy 2915 provide the basis for performing an amplification reaction. Amplifying the copies is not required and an important benefit of the disclosure is making the cDNA 2814 during the vortexing 2107 to form droplets 2401. Because DNA is much more stable than RNA, is making the cDNA 2814 during the vortexing 2107 to form droplets 2401 provides a convenient, useful, stable, and information-rich library for analyses such as expression analysis or sequencing.

It will be observed that copying the first sense copy 2915 of the cDNA 2814 using the free forward primer 2901 is the first depicted step (in this depicted embodiment) producing a molecular product not-covalently linked to the particle 2213. Copying the sense copy 2915 produces an antisense copy 2914 that is not covalently linked to the particle 2213. Of the sense copies 2915, only the first sense copy 2915 was covalently linked to the particle 2213. After copying the first sense copy, every template has a barcode ("index"). This allows droplets 2401 to be broken, after which multiplexing can proceed in bulk aqueous phase. In fact, where multiple droplets were formed and used to perform reverse transcription, each template strand may be barcoded by droplet. After "breaking the emulsion" (releasing contents from droplets into bulk aqueous phase), the same free forward primer 2901 and free reverse primer 2909 may be used to amplify, in parallel and together, any number of sense copies 2915 and antisense copies 2914 (each barcoded back to original droplet and optionally to individual strand).

Other variants and equivalents are within the scope of the disclosure.

Figure 22:
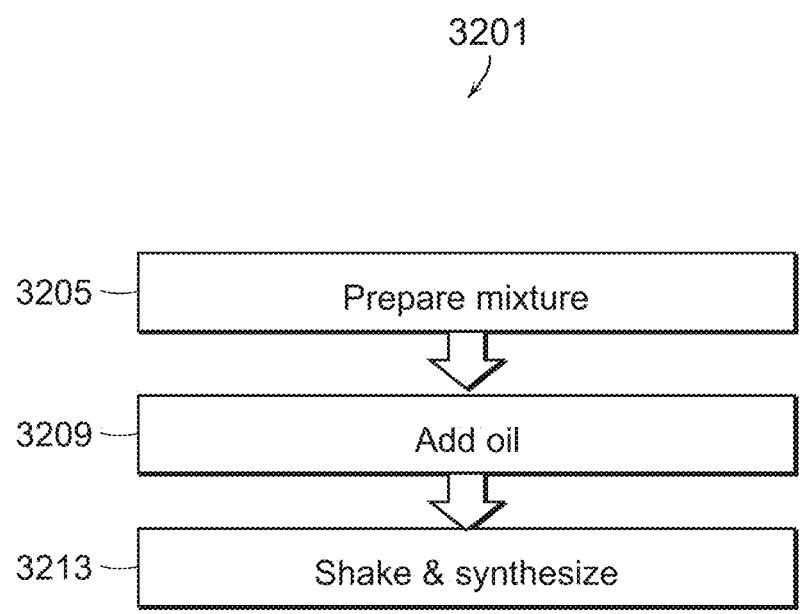
FIG. 22 diagrams a sample preparation method.

FIG. 22 diagrams a sample preparation method 3201. The method 3201 includes preparing 3205, in a sample vessel 3229, an aqueous mixture 3201 that includes nucleic acids (e.g., mRNA 2715) and polymerase enzymes (e.g., reverse transcriptase 2725). The enzymes (and other reagents) may be provided within hydrogel beads, such as beads linked to ligation-formed tripartite oligonucleotides that serve as a target capture reagent, wherein those tripartite oligonucleotides will hybridize to the nucleic acids in a downstream step. The method 3201 includes adding an oil 3225 to the sample vessel 3229. Further, the method 3201 includes shaking the sample vessel to partition the aqueous mixture into droplets 2401 surrounded by the oil and synthesizing a DNA copy 2814 of at least one of the nucleic acids with the polymerase during the shaking. The shaking and the synthesizing are performed as a single step 3213 of the method 3201. In preferred embodiments, the nucleic acids are initially in cells 2209 and the shaking step forms droplets 2401 that contain the cells 2209 and the method includes lysing the cells 2209 within the droplets 2401 to release the nucleic acids (e.g., mRNA 2715) into the droplets 2401.

Figure 23:
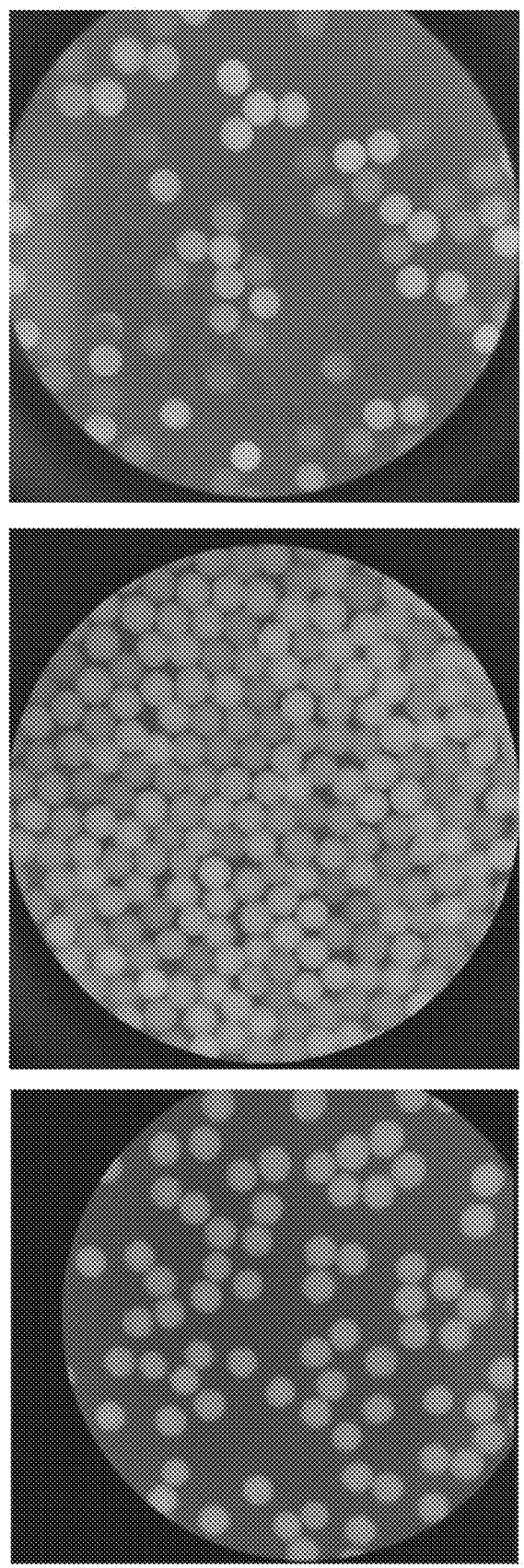
FIG. 23 shows results from performing methods of the disclosure.

FIG. 23 shows results from performing methods of the disclosure. As shown, particles with polymerase enzymes were mixed in aqueous phase with hydrogel particles and template nucleic acids under oil and with fluorescent reagents to show polymerase activity. The top panel is a photograph of what is produced when the vessel is not subject to any mixing. The middle panel shows the results of mixing at 500 rpm. The bottom panel shows what results when mixed at 1,000 rpm. It is believed that mixing at about 500 rpm promotes the uniform formation of monodisperse droplets with simultaneous successful polymerase activity. It is believed a vortexing instrument 301 may be used to establish a uniform shearing force under about 500 rpm of motion to form monodisperse droplets. The instrument 301 may be modified to include a heater to heat the aqueous mixture 201 to an optimal temperature for the polymerase (e.g., up to about 50 degrees C.). Preferably the aqueous mixture includes a plurality of template particles such as hydrogels and shaking the sample vessel causes each template particle to serve as a template in the formation of one of the droplets. For background see WO 2019/139650 A2, incorporated by reference.

Preferably in the method 3201, the nucleic acids (e.g., mRNA 2715) are initially in cells 2209 and the shaking step 3213 forms droplets wherein each of the droplet 2401 contains one template particle 2213 and one or zero cells. The method 3201 may also include lysing the cells 2209 in the droplets 2401 to release the nucleic acids into the droplets. Lysing may be done by introducing a detergent such as SDS. Beneficially, the combination of shaking at about 500 rpm, the addition of SDS, and heating to about 40 to about 50 degrees C. may be sufficient to lyse the cells 2209. Preferably, during the shaking step, the aqueous mixture is heated to a temperature that promotes reverse transcription (e.g., about 40 to about 50 degrees C.).

In some embodiments of the method 3201, the template particles are linked to capture oligos 2701, linked to the template particles at their 5' ends, wherein the 3' ends of the capture oligos include a poly-T sequence. Each of the template particles 2213 may contain some of the reverse transcriptase enzymes. During the shaking: the droplets 2401 form, cells 2209 are lysed within the droplets 2401 to release the nucleic acids, template particles 2213 capture the nucleic acids, and the polymerase enzymes synthesize the DNA copies 2814. The method 3201 is suitable for the production of a plurality of monodisperse droplets where the aqueous mixture includes a plurality of template particles, and the method comprises, after the adding step, loading the sample vessel into an instrument that performs the shaking step and wherein shaking the sample vessel causes each template particle to serve as a template in the formation of one of the droplets.

The nucleic acids may initially be in cells and the shaking step forms droplets such that each of the droplets contains one template particle and one or zero cells. Preferably the nucleic acids are mRNAs in cells in the aqueous mixture, and the droplets contain the cells; and the polymerase enzymes are provided in template particles within the aqueous mixture. The method 3201 may include—after partitioning the aqueous mixture into the droplets—lysing the cells to release the mRNAs into the droplets. The template particles may be bound to capture oligos 2701 that capture the mRNAs 2715 and prime extension reactions by which the polymerase enzymes 2725 copy the mRNAs 2715.

FIG. 24 shows components of a library member as recovered upon droplet breaking and being passed along to amplification. The tripartite oligonucleotide provides the BC1, 2, and 3 that were derived from 96 well plate split pool with diverse barcode combinations (e.g., 884,000). Some barcode sequences may be recycled at each tier (with statistically insignificant chance of collisions in final product). Preferably a minimum edit distance of 3 is used for all barcodes. The L1 and L2 sequences are fixed. C1 and C2 each refer to a GC clamp. The UMI—12 bp refers to a 12-mer unique molecular identifier. The depicted poly-T segment (e.g., 18 consecutive Ts) preferable terminates with at least one non T (IUPAC V, where the international union of pure and applied chemistry (IUPAC) has assigned "ambiguity codes" to indicate subsets of the nucleotide bases). The disclosure provides ligation-based library manufacture methods. The disclosed methods improve efficiency and quality of barcode libraries grafted to hydrogel particles compared to those form by polymerase or solid-phase synthesis. Precedent split pool chemistry relies on polymerase-based primer extension to sequentially add barcode elements to a linker adaptor grafted to the hydrogel polymer matrix. Those polymerase-based approaches required complex, and inefficient workflow prone to poor yield. Error prone barcodes due to polymerase transcription fidelity, and limited number of total barcodes in the initial design due to limitations of two-tier split pool synthesis. The present disclosure employs multiple tiers of ligation instead of polymerization to link barcoded primers on the hydrogel. These approaches eliminate barcode error due to mispolymerization. The disclosed methods require minimal manipulation between steps and are faster and more economical than polymerase methods. Methods of the disclosure may include 3 or more sequential reactions and can therefore achieve many more combinatorial barcodes while maintaining excellent separability of barcodes.

What is claimed is:

1. A method for creating a target capture reagent, the method comprising:
   dividing a plurality of beads linked to initial oligos into a first set of partitions;
   ligating partition-specific first duplexes comprising first barcodes to the initial oligos to form ligation products;
   pooling the ligation products into a pool;
   splitting the pool into a second set of partitions;
   ligating partition-specific second duplexes comprising second barcodes to the ligation products to form multi-part oligonucleotides each comprising (i) one of the initial oligos, (ii) one of the first barcodes, and (iii) one of the second barcodes;
   repeating the pooling, splitting, and ligating steps at least twice with additional sets of partition-specific duplexes and barcodes, wherein each successive repetition comprises a number of partition-specific duplexes and barcodes that is one greater than the immediate prior round of pooling, splitting, and ligating, and wherein a penultimate repeating step comprises a partition-specific duplex having two overhangs on the same strand.

2. The method of claim 1, wherein the beads comprise hydrogels.

3. The method of claim 2, wherein the beads comprise agar, glass, polyacrylamide, polystyrene, or polyethylene.

4. The method of claim 2, wherein the initial oligos are linked to the beads by acrydite linkages, click chemistry, biotin/streptavidin, silane linkage, or amide linkages.

5. The method of claim 2, wherein the method provides a plurality of beads, each linked to a plurality of copies of one of the multi-part oligonucleotides, wherein the multi-part oligonucleotides have been covalently synthesized on the beads using ligase and without using polymerase.

6. The method of claim 1, wherein the first set of partitions are wells within a multi-well plate.

7. The method of claim 6, wherein the second set of partitions are wells in a second well plate that each include copies of one of the first duplexes that hybridize to ends of the initial oligos.

8. The method of claim 1, wherein the first set of partitions and the second set of partitions are each independently selected from the group consisting of droplets of an emulsion and wells in one or more multi-well plates.

9. The method of claim 1, wherein the first set of partitions comprise wells in a multi-well plate and the second set of partitions comprise droplets of an emulsion and the splitting step comprises forming the emulsion in the wells.

10. The method of claim 1, wherein the multi-part oligonucleotides further include one or more of:
    a sequencing adaptor;
    an amplification primer binding site;
    a restriction enzyme recognition site;
    a G/C clamp;
    a unique molecular identifier; and
    a priming sequence that hybridizes to RNA.

11. The method of claim 1, wherein the initial oligos are linked to beads and the beads include one or more reagents for cell lysis or reverse transcription.

12. The method of claim 1, wherein the multi-part oligonucleotides are at least 50 to at least 1,000 bases in length.

13. The method of claim 12, wherein the at least 50 to at least 1,000 bases of length of the multi-part oligonucleotides have been synthesized without polymerase.

14. The method of claim 1, wherein each ligating step includes annealing a length of about 4 to about 8 bases of a single strand sticky end of a duplex comprising a barcode.

15. The method of claim 1, wherein the multi-part oligonucleotides have a barcode space between about a few thousand and about several hundreds of millions.

16. The method of claim 1, further comprising emulsifying the multi-part oligonucleotides with single cells in partitions and labeling cells and molecules from the cells with combinations of at least two barcodes.

17. The method of claim 1, further comprising emulsifying the multi-part oligonucleotides with single cells in partitions and labeling molecules from the cells with combinations of at least two barcodes that provide cellular barcode labels unique for each cell and UMI barcode labels unique for each molecule.

18. The method of claim 1 further comprising using the plurality of beads and the linked multi-part oligonucleotides for single cell RNA sequencing (scRNASeq).

19. A method of forming oligonucleotides on beads, the method comprising:
    performing a plurality of rounds of addition of oligos comprising two 5' overhangs onto beads covalently linked to initial oligos to form first ligation products;
    ligating an oligo comprising two overhangs on the same strand to the first ligation products to form second ligation products;
    ligating an oligo comprising a unique molecular identifier (UMI) and a poly-T primer site to the second ligation products to form oligonucleotides on beads.

\* \* \* \* \*